US008409820B2

(12) United States Patent
Imperiali et al.

(10) Patent No.: US 8,409,820 B2
(45) Date of Patent: Apr. 2, 2013

(54) KINASE SENSORS

(75) Inventors: Barbara Imperiali, Cambridge, MA (US); Elvedin Lukovic, Brooklyn, NY (US); Juan Antonio Gonzalez-Vera, Granada (ES)

(73) Assignee: Massachusetts Institute of Technology, Cambridge, MA (US)

( * ) Notice: Subject to any disclaimer, the term of this patent is extended or adjusted under 35 U.S.C. 154(b) by 161 days.

(21) Appl. No.: 12/873,065

(22) Filed: Aug. 31, 2010

(65) Prior Publication Data
US 2011/0053180 A1 Mar. 3, 2011

Related U.S. Application Data

(60) Provisional application No. 61/238,601, filed on Aug. 31, 2009.

(51) Int. Cl.
G01N 33/573 (2006.01)
C07D 401/04 (2006.01)

(52) U.S. Cl. .................................. 435/7.4; 546/167

(58) Field of Classification Search .................. None
See application file for complete search history.

(56) References Cited

U.S. PATENT DOCUMENTS

| | | | |
|---|---|---|---|
| 5,118,499 | A | 6/1992 | Theodoropulos |
| 5,455,363 | A | 10/1995 | Gosteli et al. |
| 5,854,275 | A | 12/1998 | Robinson |
| 5,912,137 | A | 6/1999 | Tsien et al. |
| 6,310,211 | B1 | 10/2001 | Vaillancourt et al. |
| 6,906,194 | B2 | 6/2005 | Imperiali et al. |
| 7,262,282 | B2 | 8/2007 | Imperiali et al. |
| 7,442,529 | B2 | 10/2008 | Imperiali et al. |
| 7,589,209 | B2 | 9/2009 | Canary et al. |
| 7,892,775 | B2 | 2/2011 | Imperiali et al. |
| 7,964,729 | B2 | 6/2011 | Imperiali et al. |
| 8,124,368 | B2 | 2/2012 | Gee |
| 2005/0080242 | A1 | 4/2005 | Imperiali et al. |
| 2005/0080243 | A1 | 4/2005 | Imperiali et al. |
| 2005/0227365 | A1 | 10/2005 | Canary et al. |
| 2006/0135746 | A1 | 6/2006 | Hosahudya et al. |
| 2006/0205760 | A1 | 9/2006 | Hartsel et al. |
| 2006/0234206 | A1 | 10/2006 | Imperiali et al. |
| 2007/0196860 | A1 | 8/2007 | Gee et al. |
| 2008/0009026 | A1 | 1/2008 | Gee |
| 2008/0050761 | A1 | 2/2008 | Imperiali et al. |
| 2008/0085529 | A1 | 4/2008 | Imperiali et al. |
| 2008/0206885 | A1 | 8/2008 | Imperiali et al. |
| 2009/0082577 | A1 | 3/2009 | Imperiali et al. |
| 2010/0168428 | A1 | 7/2010 | Imperiali et al. |
| 2011/0281290 | A1 | 11/2011 | Imperiali et al. |

FOREIGN PATENT DOCUMENTS

| | | |
|---|---|---|
| CN | 1049232 | 2/2000 |
| JP | 11335354 A | 12/1999 |
| JP | 2006213615 A | 8/2006 |
| WO | WO 01/44274 A1 | 6/2001 |
| WO | WO 2004/007461 A1 | 1/2004 |
| WO | WO 2005/037859 A2 | 4/2005 |
| WO | WO 2005/059163 A2 | 6/2005 |
| WO | WO 2006/094116 A2 | 9/2006 |
| WO | WO 2007/084968 A1 | 7/2007 |
| WO | WO 2008/016762 A1 | 2/2008 |
| WO | WO 2008/106104 A2 | 9/2008 |
| WO | WO 2008/144223 A2 | 11/2008 |
| WO | WO 2009/000965 A1 | 12/2008 |

OTHER PUBLICATIONS

Ou et al., A Sugar-Quinoline Fluorescent Chemosensor for Selective Detection of Hg2+ Ion in Natural Water, Chem. Commun. 4392-4394 (2006).*
Eftink, M.R., 66 Biophysical J. 482-501 (1994).*
International Preliminary Report on Patentability for Application No. PCT/US2010/002384 mailed Mar. 15, 2012.
Office Communication mailed Feb. 29, 2012 for U.S. Appl. No. 12/449,785.
Restriction Requirement mailed May 25, 2012 for U.S. Appl. No. 13/095,298.
International Search Report and Written Opinion for International Patent Application No. PCT/US2007/076959 mailed Oct. 7, 2008.
International Preliminary Report on Patentability for Application No. PCT/US2007/076959 mailed Mar. 12, 2009.
Supplementary European Search Report for Application No. 07872278.2 dated Apr. 7, 2011.
Invitation to Pay Additional Fees for Application No. PCT/US2008/002485 mailed Aug. 28, 2008.
International Search Report and Written Opinion for International Patent Application No. PCT/US2008/002485 mailed Nov. 7, 2008.
International Preliminary Report on Patentability for Application No. PCT/US2008/002485 mailed Sep. 3, 2009.
International Search Report and Written Opinion for International Patent Application No. PCT/US2004/032733 Oct. 28, 2005.
International Preliminary Report on Patentability for Application No. PCT/US2004/032733 mailed Apr. 20, 2006.
International Search Report and Written Opinion for International Patent Application No. PCT/US2010/002384 mailed Dec. 16, 2010.
Office Action for U.S. Appl. No. 11/511,050 mailed Jun. 17, 2009.
Office Action for U.S. Appl. No. 11/511,050 mailed Jan. 28, 2010.
Office Action for U.S. Appl. No. 11/511,050 mailed Aug. 11, 2010.
Notice of Allowance for U.S. Appl. No. 11/511,050 mailed Jan. 27, 2011.
Office Action for U.S. Appl. No. 11/106,349 mailed Mar. 8, 2007.
Office Action for U.S. Appl. No. 11/106,349 mailed Aug. 22, 2007.
Notice of Allowance for U.S. Appl. No. 11/106,349 mailed Dec. 27, 2007.
Notice of Allowance for U.S. Appl. No. 11/106,349 mailed Jun. 23, 2008.

(Continued)

Primary Examiner — Janet Andres
Assistant Examiner — Timothy R Rozof
(74) Attorney, Agent, or Firm — Wolf, Greenfield & Sacks, P.C.

(57) ABSTRACT

The present invention generally relates to compositions and methods for determining kinase activity. In some cases, the compositions comprise a triazole heterocycle. In some embodiments, the compositions comprise a quinoline moiety. In one aspect, the present invention is directed to compositions that undergo chelation-enhanced fluorescence (CHEF). In some cases, the compositions may have fluorescence emission spectra with peak maxima greater than 490 nm. The compositions of the present invention can be used, in certain embodiments, to detect phosphorylated substrates and biological processes such as phosphorylation events.

11 Claims, 19 Drawing Sheets

OTHER PUBLICATIONS

Office Action for U.S. Appl. No. 10/681,427 mailed Sep. 15, 2004.
Notice of Allowance for U.S. Appl. No. 10/681,427 mailed Feb. 17, 2005.
Restriction Requirement for U.S. Appl. No. 10/819,587 mailed Jul. 13, 2006.
Office Action for U.S. Appl. No. 10/819,587 mailed Oct. 18, 2006.
Notice of Allowance for U.S. Appl. No. 10/819,587 mailed Feb. 13, 2007.
Office Action for U.S. Appl. No. 11/801,921 mailed Oct. 8, 2009.
Notice of Allowance for U.S. Appl. No. 11/801,921 mailed Apr. 2, 2010.
Notice of Allowance for U.S. Appl. No. 11/801,921 mailed Oct. 6, 2010.
[No Author Listed] A list of peptides that can be phosphorylated (and the corresponding Kinases) found at online at www.neb.com/neb/tech/tech_resource/protein_tools/substraye_recognition.html. Last Accessed on Sep. 26, 2003.
Barluenga et al., Easy and regioselective synthesis of highly functionalized o-quinodimethide precursors from fischer carbene complexes and Isocyanides. Chem. Eur. J. 2002; 8(18):4149-4163.
Blake et al., A new pyridine-based 12-membered macrocycle functionalised with different fluorescent subunits; coordination chemistry towards Cu(II), Zn(II), Cd(II), Hg(II), and Pb(II). Dalton Trans. Sep. 7, 2004;(17):2771-9. Epub Aug. 6, 2004.
Brown et al., Matrix metalloproteinase inhibitors containing a (carboxyalkyl)amino zinc ligand: modification of the P1 and P2' residues. J Med Chem. Mar. 4, 1994;37(5):674-88.
Cacialli et al., Naphthalimide side-chain polymers for organic light-emitting diodes: band-offset engineering and role of polymer thickness. J Appl Phys. 1998;83(4):2343-2356.
Carrigan et al., The engineering of membrane-permeable peptides. Anal Biochem. Jun. 15, 2005;341(2):290-8.
Chen et al., Biosensors of protein kinase action: from in vitro assays to living cells. Biochim Biophys Acta. Mar. 11, 2004;1697(1-2):39-51.
Chen et al., Design and synthesis of a fluorescent reporter of protein kinase activity. J Am Chem Soc. Apr. 17, 2002;124(15):3840-1.
Cohen et al., Probing protein electrostatics with a synthetic fluorescent amino acid. Science. May 31, 2002;296(5573):1700-3.
Goncalves, Fluorescent labeling of biomolecules with organic probes. Chem Rev. Jan. 2009;109(1):190-212.
Gonzalez-Vera et al., Synthesis of red-shifted 8-hydroxyquinoline derivatives using click chemistry and their incorporation into phosphorylation chemosensors. J Org Chem. Oct. 2, 2009;74(19):7309-14.
Gopi et al., Structural determinants for affinity enhancement of a dual antagonist peptide entry inhibitor of human immunodeficiency virus type-1. J Med Chem. May 8, 2008;51(9):2638-47.
Grabchev et al., Synthesis and properties of fluorescent 1,8-naphthalimide dyes for application in liquid crystal displays. J Mater Chem. 2000(10):1291-1296.
Higashi et al., Imaging of cAMP-dependent protein kinase activity in living neural cells using a novel fluorescent substrate. FEBS Lett. Sep. 1, 1997;414(1):55-60.
Hofmann et al., Fluorescent monitoring of kinase activity in real time: development of a robust fluorescence-based assay for Abl tyrosine kinase activity. Bioorg Med Chem Lett. Dec. 17, 2001;11(24):3091-4.
Jotterand et al., Asymmetric synthesis of a new 8-hydroxyquinoline-derived alpha-amino acid and its incorporation in a peptidylsensor for divalent zinc. J Org Chem. May 4, 2001;66(9):3224-8.
Knor et al., Synthesis of novel 1,4,7,10-tetraazacyclodecane-1,4,7,10-tetraacetic acid (DOTA) derivatives for chemoselective attachment to unprotected polyfunctionalized compounds. Chem Eur J. 2007;13(21):6082-6089.
Kurokawa et al., A pair of fluorescent resonance energy transfer-based probes for tyrosine phosphorylation of the CrkII adaptor protein in vivo. J Biol Chem. Aug. 17, 2001;276(33):31305-10. Epub Jun. 13, 2001.
Lawrence, Chemical probes of signal-transducing proteins. Acc Chem Res. Jun. 2003;36(6):401-9.

Lee et al., Synthesis of 2,3,8-trisubstituted 7H-Isoindolo[5,6-g]quinoxaline-5,7,9,11(8H)-tetraones. Heterocycles. 2004;63(4):819-426.
Lindgren et al., Cell-penetrating peptides. Trends Pharmacol Sci. Mar. 2000;21(3):99-103.
Lukovic et al., Recognition-domain focused chemosensors: versatile and efficient reporters of protein kinase activity. J Am Chem Soc. Sep. 24, 2008;130(38):12821-7. Epub Aug. 29, 2008.
McLlroy et al., A continuous fluorescence assay for protein kinase C. Anal Biochem. May 15, 1991;195(1):148-52.
Moder et al., Defined dimensional alterations in enzyme substrates. Synthesis and enzymatic evaluation of some lin-naphthopurines. J. Am. Chem. Soc. 1982;104:2613-2624.
Montes et al., Effective manipulation of the electronic effects and its influence on the emission of 5-substituted tris(8-quinolinolate) aluminum(III) complexes. Chemistry. Jun. 2, 2006;12(17):4523-35.
Nagai et al., A fluorescent indicator for visualizing cAMP-induced phosphorylation in vivo. Nat Biotechnol. Mar. 2000;18(3):313-6.
Newton et al., Protein kinase C: structural and spatial regulation by phosphorylation, cofactors, and macromolecular interactions. Chem Rev. Aug. 2001;101(8):2353-64.
Nishikawa et al., Determination of the specific substrate sequence motifs of protein kinase C isozymes. J Biol Chem. Jan. 10, 1997;272(2):952-60.
Ohuchi et al., A fluorescent-labeled oligopeptide for monitoring PKA-mediated phosphorylation. Analyst. Nov. 2000;125(11):1905-7.
Okamoto et al., A supported epoxidation catalyst for nucleophilic olefins. Tetrahedron Letters. 1988;29(9):971-4. Abstract.
Pantoja et al., Synthesis and use of fluorescent molecular probes for measuring cell-surface enzymatic oxidation of amino acids and amines in seawater. Analytical Biochemistry 1993;211:210-218.
Pinna et al., Phosphorylated synthetic peptides as tools for studying protein phosphatases. Biochim Biophys Acta. Jul. 21, 1994;1222(3):415-31.
Post et al., A genetically engineered, protein-based optical biosensor of myosin II regulatory light chain phosphorylation. J Biol Chem. Apr. 29, 1994;269(17):12880-7.
Pozarentzi et al., The first benzodiazepine o-quinodimethane: generation and Diels-Alder reactions. Tetrahedron Letters. 2003;44:2007-9.
Rothmann et al., Chemical approaches for investigating phosphorylation in signal transduction networks. Trends Cell Biol. Sep. 2005;15(9):502-10.
Royzen et al., A sensitive probe for the detection of Zn(II) by time-resolved fluorescence. J Am Chem Soc. Mar. 29, 2006;128(12):3854-5.
Sainlos et al., Synthesis of anhydride precursors of the environment-sensitive fluorophores 4-DMAP and 6-DMN. Nat Protoc. 2007;2(12):3219-25.
Sainlos et al., Tools for investigating peptide-protein interactions: peptide incorporation of environment-sensitive fluorophores via on-resin derivatization. Nat Protoc. 2007;2(12):3201-9.
Sainlos et al., Tools for investigating peptide-protein interactions: peptide incorporation of environment-sensitive fluorophores through SPPS-based 'building block' approach. Nat Protoc. 2007;2(12):3210-8.
Sato et al., Fluorescent indicators for imaging protein phosphorylation in single living cells. Nat Biotechnol. Mar. 2002;20(3):287-94.
Shults et al., Optimal Sox-based fluorescent chemosensor design for serine/threonine protein kinases. Anal Biochem. May 15, 2006;352(2):198-207. Epub Mar. 20, 2006.
Shults et al., A multiplexed homogeneous fluorescence-based assay for protein kinase activity in cell lysates. Nat Methods. Apr. 2005;2(4):277-83. Epub Mar. 23, 2005.
Shults et al., Modular and tunable chemosensor scaffold for divalent zinc. J Am Chem Soc. Sep. 3, 2003;125(35):10591-7.
Shults et al., Versatile fluorescence probes of protein kinase activity. J Am Chem Soc. Nov. 26, 2003;125(47):14248-9.
Stevenson et al., Defined dimensional alterations in enzyme substrates. lin-naphthoadenine and lin-naphthoadenosine. J. Org. Chem. 1984;49:2158-2164.

Su et al., Syntheses and Metal Ion Complexation of Novel 8-Hydroxyquinoline-Containing Diaza-18-Crown-6 Ligands and Analogues. J Org Chem. Nov. 26, 1999;64(24):8855-8861.

Suzuki et al., Preparation and crystal structures of tetracyanoquinodimethans fused with [1,2,5]selenadiazole units. Chemistry Letters. 1987:2285-2288.

Ting et al., Genetically encoded fluorescent reporters of protein tyrosine kinase activities in living cells. Proc Natl Acad Sci U S A. Dec. 18, 2001;98(26):15003-8.

Vazquez et al., A new environment-sensitive fluorescent amino acid for Fmoc-based solid phase peptide synthesis. Org Biomol Chem. Jul. 21, 2004;2(14):1965-6.

Vazquez et al., Photophysics and biological applications of the environment-sensitive fluorophore 6-N,N-dimethylamino-2,3-naphthalimide. J Am Chem Soc. Feb. 2, 2005;127(4):1300-6. Supporting Information p. 1-26.

Venkatraman et al., Fluorogenic probes for monitoring peptide binding to class II MHC proteins in living cells. Nature Chemical Biology. Apr. 2007; 3 (4): 222-228.

Violin et al., A genetically encoded fluorescent reporter reveals oscillatory phosphorylation by protein kinase C. J Cell Biol. Jun. 9, 2003;161(5):899-909. Epub Jun. 2, 2003.

Wadia et al., Protein transduction technology. Curr Opin Biotechnol. Feb. 2002;13(1):52-6.

Walkup et al., Stereoselective synthesis of florescent a-amino acids containing oxine (8-hydroxyquinoline and their peptide incorporation in chemosensors for divalent zinc. J Org Chem. 1998; 63(19):6727-6731.

Wang et al., Phosphorylation-driven protein-protein interactions: a protein kinase sensing system. J Am Chem Soc. Jun. 1, 2005;127(21):7684-5.

Wang et al., Self-reporting fluorescent substrates of protein tyrosine kinases. J Am Chem Soc. Feb. 15, 2006;128(6):1808-9.

Weber et al., Synthesis and spectral properties of a hydrophobic fluorescent probe: 6-propionyl-2-(dimethylamino)naphthalene. Biochemistry. Jul. 10, 1979;18(14):3075-8.

Wright et al., Fluorometric assay for adenosine 3',5'-cyclic monophosphate-dependent protein kinase and phosphoprotein phosphatase activities. Proc Natl Acad Sci U S A.1981 ct;78(10):6048-50.

Yeh et al., Real time visualization of protein kinase activity in living cells. J Biol Chem. Mar. 29, 2002;277(13):11527-32. Epub Jan. 14, 2002.

Zhang et al., Genetically encoded reporters of protein kinase A activity reveal impact of substrate tethering. Proc Natl Acad Sci U S A. Dec. 18, 2001;98(26):14997-5002.

Zhang et al., New fluorescent conjugates of uridine nucleoside and substituted 1,8-naphthalimide: synthesis, weak interactions and solvent effects onsSpectra. Monatshefte fur Chemie Chemical Monthly 2003;134:393-402.

Office Communication mailed Sep. 17, 2012 for U.S. Appl. No. 13/095,298.

Office Communication mailed Jul. 13, 2012 for U.S. Appl. No. 12/449,785.

\* cited by examiner

| Complex | R¹ | R² | $\lambda_{ex}$ (nm) | $\lambda_{em}$ (nm) | Φ |
|---|---|---|---|---|---|
| 1 | SO$_2$N(CH$_3$)$_2$ | CH$_3$ | 360 | 485 | 0.342 |
| 2 | CHO | CH$_3$ | 373 | 460 | 0.597 |
| 3 | CN | CH$_3$ | 362 | 485 | 0.276 |
| 4 | COCH$_3$ | CH$_3$ | 370 | 465 | 0.168 |
| 5 | COCH$_2$Cl | CH$_3$ | 373 | 460 | 0.034 |
| 6 | CO$_2$H | CH$_3$ | 362 | 505 | 0.004 |
| 7 | CO-Ph | H | 375 | 485 | 0.002 |

| Entry | Target kinase | Location of the chromophore | Peptide Sequence | Fold Fluorescence Increase | |
|---|---|---|---|---|---|
| 1 | MK2 | C | Ac-AHLQRQLS*I-C(Sox)-HH-CONH$_2$ | 4.4±0.2 | SEQ ID NO:1 |
| 2 | MK2 | C | Ac-AHLQRQLS*I-C(Clk)-HH-CONH$_2$ | 2.1±0.3 | SEQ ID NO:2 |
| 3 | Src | N | Ac-AEE-C(Sox)-IY*GEFEAKKKK-CONH$_2$ | 2.0±0.1 | SEQ ID NO:3 |
| 4 | Src | N | Ac-AEE-C(Clk)-IY*GEFEAKKKK-CONH$_2$ | 2.4±0.2 | SEQ ID NO:4 |
Fig. 5
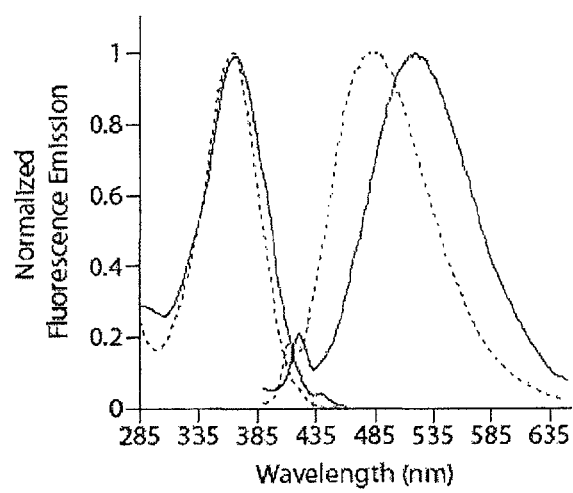
Fig. 6A
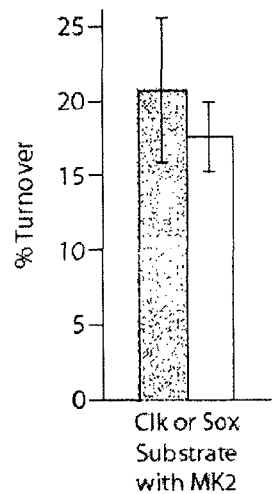
Fig. 6B

| Kinase | Peptide | Peptide Sequence | Mol. Formula | HPLC $t_R$ (min) | [M] Calcd. | [M+H]+ found | |
|---|---|---|---|---|---|---|---|
| MK2 | P1 | Ac-AHLQRQLSI-CSox-HH-CONH$_2$ | | | | | SEQ ID NO:5 |
| | | Ac-AHLQRQLpSI-CSox-HH-CONH$_2$ | | | | | SEQ ID NO:1 |
| | P2 | Ac-AHLQRQLSI-CClk-HH-CONH$_2$ | $C_{81}H_{113}BrN_{28}O_{17}S$ | 21.32 | 1862.91 | 1863.38 | SEQ ID NO:6 |
| | | Ac-AHLQRQLpSI-CClk-HH-CONH$_2$ | $C_{81}H_{113}BrN_{28}O_{20}PS$ | 23.45 | 1942.89 | 1943.22 | SEQ ID NO:2 |
| Src | P3 | Ac-AEE-CSox-IYGEFEAKKKK-CONH$_2$ | | | | | SEQ ID NO:7 |
| | | Ac-AEE-CSox-IpYGEFEAKKKK-CONH$_2$ | | | | | SEQ ID NO:3 |
| | P4 | Ac-AEE-CClk-IYGEFEAKKKK-CONH$_2$ | $C_{99}H_{139}BrN_{24}O_{26}S$ | 22.00 | 2193.28 | 2194.45 | SEQ ID NO:8 |
| | | Ac-AEE-CClk-IpYGEFEAKKKK-CONH$_2$ | $C_{99}H_{140}BrN_{24}O_{29}PS$ | 21.86 | 2273.26 | 2274.96 | SEQ ID NO:4 |

Fig. 7

| Compound | $\lambda_{ex}$ (nm) | $\lambda_{em}$ (nm) | Φ |
|---|---|---|---|
| 10a | 371 | 522 | 0.033 |
| 10b | 370 | 525 | 0.041 |
| 10c | 367 | 523 | 0.043 |
| 10d | 365 | 525 | 0.071 |
| 10e | 365 | 520 | - |
| 10f | 365 | 525 | - |
| 10g | 365 | 525 | - |
| 10h | 365 | 510 | - |
| 10i | 375 | 525 | 0.067 |
| 10j | 365 | 525 | - |
| 10k | 365 | 525 | - |
| 10l | 360 | 520 | - |
| 10m | 360 | 525 | - |
| 10n | 365 | 515 | - |
| 10o | 360 | 510 | - |
| 10p | 360 | 520 | - |
| 10q | 365 | 515 | - |
| 10r | 360 | 520 | - |
| 10s | 360 | 530 | - |
| 10t | 360 | 525 | - |
| 10u | 375 | 525 | 0.111 |
| 10v | 365 | 520 | - |

Fig. 8

KINASE SENSORS

RELATED APPLICATIONS

This application claims the benefit of U.S. Provisional Patent Application Ser. No. 61/238,601, filed Aug. 31, 2009, entitled "Kinase Sensors," by Imperiali et al., which is incorporated herein by reference.

STATEMENT REGARDING FEDERALLY SPONSORED RESEARCH OR DEVELOPMENT

This invention was made with government support under Grant No. GM064346, awarded by the National Institutes of Health. The government has certain rights in this invention.

FIELD OF INVENTION

The present invention generally relates to compositions and methods for determining phosphorylation activity.

BACKGROUND

The ubiquitous process of protein phosphorylation is central to signal transduction and regulation in living organisms. By catalyzing transfer of the γ-phosphoryl group of ATP to the side chains of serine, threonine, and/or tyrosine, protein kinases play an important role in regulating many aspects of cellular function in eukaryotes, including proliferation, cell cycle, metabolism, transcription, and apoptosis. Not surprisingly, protein kinases have also emerged as attractive targets for drug discovery, since many are associated with a wide variety of diseases, from cancer to inflammation. Thus, tools that allow for facile monitoring of kinase activity are in great demand in both pharmaceutical and academic settings.

SUMMARY OF THE INVENTION

The present invention provides improvements in compositions and methods for determining kinase activity, in particular, protein kinase activity. The invention involves compositions and techniques that facilitate fluorescence-based sensing of kinase activity at electromagnetic radiation emission wavelengths longer (lower in energy) than provided by the prior art. Emission at longer wavelengths provides at least two advantages. First, longer emission wavelengths can result in easier detection because the sensing emission wavelength is separated from, or at least less obscured by or overlapping with, background signals typically present in an environment where sensing is desired. Second, emission at longer wavelengths, whether in vivo, or in vitro in the presence of tissue, can reduce what might otherwise cause damage to tissue and/or other species because of the lower energy of emission and/or lower adsorption of the emission by tissue and/or other species. The invention involves development of a class of novel compositions of matter which can form the basis of sensing compositions and techniques. The invention also provides compositions and techniques for kinase sensing including a class of molecules some members of which are known in the prior art but are not known for use in kinase sensing. The invention also provides the general ability to engage in kinase sensing via emission as longer wavelengths than is known in the prior art.

In some embodiments, composition are provided. The compound may comprise a compound having a structure as in formula (I):

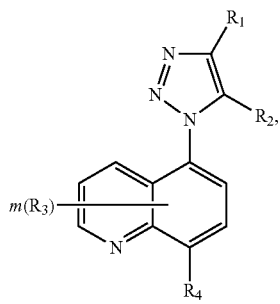

(I)

where $R_1$ and $R_2$ are each independently hydrogen or aryl, or where $R_1$ and $R_2$ together with the carbon atoms of the triazole ring to which they are connected form a ring; $R_3$ is independently hydrogen, alkyl, aryl, halo, or hydroxyl, amino, thiol, sulfonic acid, sulfonamide or a substituted derivative thereof, wherein $R_3$ can substitute any open valence of any ring within structure (I); m is 1, 2, 3, 4, or 5; and $R_4$ is hydroxyl, amino, thiol, or a substituted derivative thereof.

In some embodiments, the compound may have a structure as in formula (II):

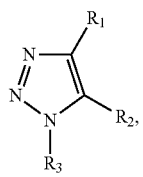

(II)

where $R_1$ and $R_2$ are each independently hydrogen or aryl, or where $R_1$ and $R_2$ together with the carbon atoms of the triazole ring to which they are connected form a ring; and $R_3$ comprises i) a species capable of fluorescing, and ii) a protein kinase substrate or at least one amino acid.

Various methods are also provided. In some embodiments, the method comprises determining phosphorylation of a protein kinase substrate using fluorescence of a composition, wherein the composition has a fluorescence emission maximum greater than 490 nm. In some embodiments, the method comprises determining phosphorylation of a protein kinase substrate using fluorescence of a composition, wherein the composition has a fluorescence extinction coefficient greater than $1000 \text{ M}^{-1} \text{ cm}^{-1}$ at a fluorescence emission wavelength greater than 490 nm. In some embodiments, the method comprises determining phosphorylation of a protein kinase substrate using fluorescence of any composition described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more applications incorporated by reference include conflicting and/or inconsistent disclosure with respect to each other, then the later-filed application shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. In the figures:

FIG. 5 shows a table of substrate sequences of RDF chemosensors and fluorescence increases.

FIG. 6 shows (a) spectral characterization and (b) enzymatic evaluation of various Clk-based substrates.

FIG. 7 shows a table of characterization data for various peptides. The synthesis and characterization of peptides P1 and P3 has been described. Reported retention times ($t_R$) and HPLC conditions are from analytical runs. Method: 5% B (5 min) followed by an increase to 15% B (1 min) and a linear gradient to 15-45% B (30 min). The [M+H]$^+$ data was collected on a MALDI-TOF mass spectrometer.

FIG. 8 shows a table of fluorescence properties for various compositions described herein.

Figure 1:
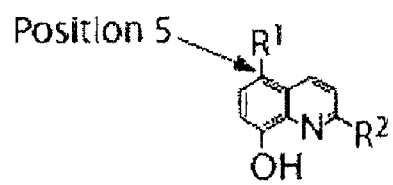
FIG. 1 shows a table of fluorescence data for various prior art compositions.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to compositions and methods for determining kinase activity, using electromagnetic emission at longer wavelengths (lower in energy) than previously reported.

As noted above, various classes of compositions are provided, including those that can undergo chelation-enhanced fluorescence (CHEF). In some cases, the compositions may have fluorescence emission spectra with peak maxima greater than 490 nm, and/or a fluorescence extinction coefficient greater than 1000 M$^{-1}$ cm$^{-1}$ at a fluorescence emission wavelength greater than 490 nm. The compositions of the present invention can be used, in certain embodiments, to detect phosphorylated substrates and biological processes such as phosphorylation events. One class of compositions of the invention includes a triazole hetrocycle-based structure coupled to a species capable of fluorescing, where the triazole hetrocycle-based structure affects electromagnetic radiation emission such that longer wavelength, lower energy emission results. Another class of molecules includes a quinoline moiety based structure that provides the molecule with fluorescent capability, which can be used as a kinase sensor at longer wavelength/lower energy emission as described herein.

In some embodiments, the present invention provides compositions for the detection of a phosphorylated substrate. The composition may comprise a luminescent species, such as a species capable of generating a fluorescence emission (e.g., fluorophore). The fluorophore may be any species capable of generating a fluorescent signal upon exposure to an external source of energy (e.g., electromagnetic radiation, a chemical reagent, etc.). As noted above, some embodiments may advantageously provide compositions which exhibit a red-shifted fluorescence emission, i.e., a fluorescence emission shifted to longer, lower energy wavelengths. For example, the species may comprise a group which extends the pi-conjugation of the luminescent species, thereby reducing the pi-pi* gap and causing a red-shift in emission. In some cases, the luminescent species may include one or more electron-rich groups, such as amino, hydroxy, alkoxy, acylamino, acyloxy, alkyl, halide, electron-rich aryl groups (e.g., triazoles), and the like, such that the composition exhibits fluorescence excitation and emission at longer wavelengths.

In some cases, the composition has a fluorescence emission maximum greater than 490 nm, greater than 500 nm, greater than 510 nm, greater than 520 nm, greater than 530 nm, greater than 540 nm, greater than 550 nm, greater than 600 nm, or, in some cases, greater.

In some embodiments, the composition may also include a phosphorylation site, including a hydroxyl group and hydroxyl-containing amino acid residues, such as serine, threonine and tyrosine. Without wishing to be bound by theory, a phosphorylated sensor or composition may have increased affinity for a metal, such as $Mg^{2+}$, and upon binding the metal, the fluorescence of the sensor may be enhanced by a phenomenon known in art as chelation-enhanced fluorescence (CHEF). In some embodiments, the enhanced fluorescence may be measured and used to monitor and/or quantify phosphorylation, as discussed in more detail below.

In one set of embodiments, the composition may comprise a compound comprising a triazole ring. For example, the composition may comprise a compound having a structure as in formula (I),

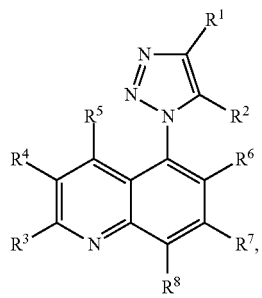

wherein $R^1$ and $R^2$ can be the same or different and are each independently hydrogen, alkyl, aryl, heteroaryl, carbocyclic, or heterocyclic, or where $R_1$ and $R_2$ are joined together to form a ring; $R^3$, $R^4$, $R^5$, $R^6$, and $R^7$ can be the same or different and are each independently hydrogen, alkyl, aryl, heteroaryl, halo, hydroxyl, amino, thiol, sulfonic acid, sulfonamide, or a substituted derivative thereof; and $R^8$ is hydroxyl, amino, thiol, or a substituted derivative thereof. In some cases, $R_1$ and $R_2$ are each independently hydrogen, aryl, or heterocyclyl, such as phenyl, pyridinyl, imidazolyl, thiophenyl, naphthyl, or the like, any of which may be optionally substituted. In some embodiments, $R_1$ and $R_2$ are joined together with the carbon atoms of the triazole ring to which they are connected form a ring, including a carbocyclic or heterocyclic ring, which may optionally include one or more alkenyl or alkynyl groups. The ring may be, for example, a 5-, 6-, 7-, or 8-membered ring, optionally substituted.

In some embodiments, at least one of $R^3$, $R^4$, $R^5$, $R^6$, and $R^7$ comprises at least one amino acid or a protein kinase substrate. In some embodiments, at least one of $R^3$, $R^4$, $R^5$, $R^6$, and $R^7$ contains a functional group capable of reacting with a molecule such as an amino acid or protein kinase substrate. In some cases, $R^4$, $R^5$, $R^6$, and $R^7$ are each hydrogen. In some embodiments, $R^8$ is hydroxyl. In certain embodiments, $R^1$ may be cyclohexenyl, phenyl, bis-trifluoromethylphenyl, bromophenyl, chlorophenyl, fluorophenyl, tosyl, cyanophenyl, methoxyphenyl, toluoyl, pentylphenyl, imidazoyl, thiophenyl, aminophenyl, pyridinyl, dimethylaminophenyl, naphthalenyl, methoxynaphthalenyl, etc. In some instances, $R^2$ is hydrogen. In some examples, $R^3$ comprises at least one amino acid or a protein kinase substrate.

In another set of embodiments, the composition may a comprise compound having a structure as in formula (II),

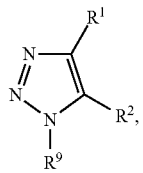

wherein $R^1$ and $R^2$ can be the same or different and are each independently hydrogen, alkyl, aryl, heteroaryl, carbocyclic, or heterocyclic, or where $R_1$ and $R_2$ are joined together to form a ring; and $R^9$ comprises (i) a fluorophore or a species capable of fluorescing and (ii) a protein kinase substrate or at least one amino acid. In some embodiments, the species may be a compound capable of chelation-enhanced fluorescence, such as a quinoline structure. The protein kinase substrate or at least one amino acid may be a substituent of the species capable of fluorescing and may be connected directly or with a linker (i.e., a hydrocarbon chain, polyethyleneglycol, a polymer, etc.).

In another embodiment, a composition of the present invention may comprise a compound having a structure as in formula (III),

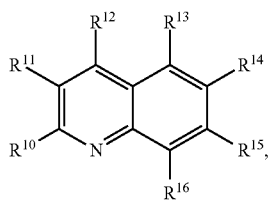

wherein $R^{10}$, $R^{11}$, $R^{12}$, $R^{13}$, $R^{14}$, $R^{15}$, and $R^{16}$ can be the same or different and are each independently hydrogen, alkyl, alkenyl, alkynyl, aryl, heteroaryl, halo, hydroxyl, amino, thiol, sulfonic acid, sulfonamide, azido, or a substituted derivative thereof.

In some embodiments, at least one of $R^{10}$, $R^{11}$, $R^{12}$, $R^{13}$, $R^{14}$, $R^{15}$, and $R^{16}$ may be selected to be conjugated (e.g., pi-conjugated) with the quinoline moiety of formula (III). In some cases, at least one of $R^{10}$, $R^{11}$, $R^{12}$, $R^{13}$, $R^{14}$, $R^{15}$, and $R^{16}$ comprises a protein kinase substrate or at least one amino acid. In some cases, at least one of $R^{10}$, $R^{11}$, $R^{12}$, $R^{13}$, $R^{14}$, $R^{15}$, and $R^{16}$ comprises a functional group capable of forming a chemical bond with a molecule, such as a protein kinase substrate or amino acid. In some cases, $R^{10}$ comprises a protein kinase substrate or at least one amino acid. In some cases, at least one of $R^{10}$, $R^{11}$, $R^{12}$, $R^{13}$, $R^{14}$, $R^{15}$, and $R^{16}$ is hydroxyl, amino, thiol, or a substituted derivative thereof. For example, in some embodiments, $R^{16}$ is hydroxyl, amino, thiol, or a substituted derivative thereof. In some instances, $R^{13}$ comprises a group (e.g., a triazole group) that is conjugated with the quinoline moiety of formula (III).

In some embodiments, $R^{13}$ is alkynyl, and $R^{10}$ comprises a protein kinase substrate or at least one amino acid.

In one embodiment, the compound has the following structure,

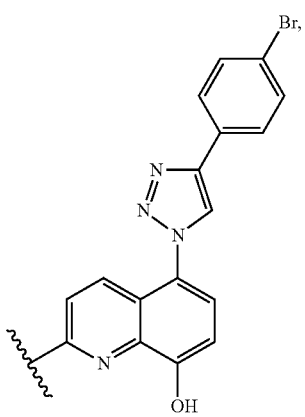 [SMILES: *c1ccc2c(-n3cc(-c4ccc(Br)cc4)nn3)ccc(O)c2n1]

wherein ᔕᔕᔕ comprises a protein kinase substrate or at least one amino acid.

Some embodiments of the invention may include one or more groups that can be further altered (e.g., reacted) such that a new functional group (e.g., atom or chemical group) is formed. In one set of embodiments, the composition may include a group capable of reacting via a 1,3-dipolarcycloaddition reaction, i.e., via "click chemistry." For example, the composition may comprise a dipolarophile group (e.g., an alkyne) that is reacted with a 1,3-dipolar compound. Alternatively, the composition may comprise a 1,3-dipolar compound (e.g., an azido group) that is reacted with a dipolarophile. The 1,3-dipolar cycloaddition reaction may be performed under conditions that may be unreactive to the remainder of the compound, other than the dipolarophile or 1,3-dipolar compound. In an illustrative embodiment, the composition may contain an azido group, which may be further reacted with an alkyne to form a triazole group. In some embodiments, the molecule capable of fluorescing may comprise an azido group, where the azido group may be reacted with an alkynyl-containing compound to generate a fluorophore. Such a strategy may be useful, for example, for incorporating compositions described herein into a peptide structure, as described more fully below. Those of ordinary skill in the art would be able to select the appropriate reaction conditions and additives suitable for a particular 1,3-dipolar cycloaddition reaction. Methods for performing 1,3-dipolar cycloaddition reactions are also described, for example, in *Synthetic Applications of 1,3-Dipolar Cycloaddition Chemistry Toward Heterocycles and Natural Products*, A. Padwa, W. H. Pearson, Wiley-Interscience, 2002, the contents of which are incorporated herein by reference.

In some cases, intermediate compounds comprising azido groups are provided. For example, a composition may comprise a compound having a structure as in formula (III), wherein at least one of $R^{10}$, $R^{11}$, $R^{12}$, $R^{13}$, $R^{14}$, $R^{15}$, and $R^{16}$ is azido, and at least one of $R^{10}$, $R^{11}$, $R^{12}$, $R^{13}$, $R^{14}$, $R^{15}$, and $R^{16}$ is hydroxyl, amino, thiol, or a substituted derivative thereof, and/or is capable of reacting with a functional group of an amino acid.

In some embodiments, the intermediate compound has the following formula,

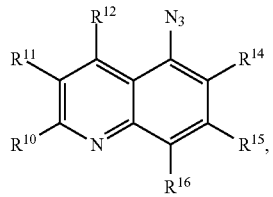

wherein $R^{10}$, $R^{11}$, $R^{12}$, $R^{14}$, $R^{15}$, and $R^{16}$ are as defined above.

Some embodiments of the invention provide proteins or peptides substituted with compositions as described herein. For instance, an amino acid residue on a protein, such as cysteine, aspartic acid, glutamic acid, or lysine, may be well-suited for reaction with any of the compounds described herein. Such substituted peptides may be useful for a wide variety of applications, such as kinase sensing or other fluorescent sensing applications, as the compound may retain substantially all of its fluorescence even when attached to the peptide. For example, the substituted peptides may be useful as fluorescent probes for various biological applications. As a specific example, compounds such as those of formulae (I), (II), and/or (III), can be attached to peptides using standard peptide synthesis methods (solid phase or solution phase), such as those described in, for example, *Fmoc Solid Phase Peptide Synthesis—A Practical Approach*, Oxford University Press, 2003, Eds W. C. Chan and P. D. White (ISBN 0 19 963 724 5) and *The Chemical Synthesis of Peptides*, Clarendon Press, Oxford, 1994, Jones, J. (ISBN 0 19 855839 2).

Compounds of the present invention, including peptides substituted with compositions described herein, can be used in a various methods (e.g., methods for determining kinase activity). Methods for the determination of analytes may comprise exposure of a composition described herein to a sample suspected of containing an analyte, and, if present, the analyte interacts with the composition to cause a change in a signal of the composition (e.g., an optical signal). As used herein, the term "determining" generally refers to the analysis of a species or signal, for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction. In some cases, determination of the analyte is performed in vivo. In some cases, determination of the analyte is performed in vitro.

In some embodiments, the analyte may interact with the composition to cause a change in affinity (e.g., binding affinity) of the composition for another species (e.g., metal ion) and/or a change in an optical signal of the composition, which may then determine the analyte. In some cases, the method may involve determining phosphorylation of a protein kinase substrate using fluorescence of the compositions described herein, wherein the composition has a fluorescence emission maximum greater than 490 nm. In some cases, the composition may have a fluorescence extinction coefficient greater than 1000 $M^{-1}$ $cm^{-1}$ at a fluorescence emission wavelength greater than 500 nm. For example, the composition may include a protein kinase substrate having a first fluorescence emission, wherein interaction of the composition with an analyte generates a determinable change or shift in the fluorescence emission, thereby indicating the presence and/or amount of the analyte.

In some embodiments, the method may comprise providing a composition as described herein, wherein the composition comprises a phosphorylation site and a compound capable of fluorescing upon chelation of a metal, and exposing the composition to a sample comprising $Mg^{2+}$, a phosphoryl donor (e.g., ATP), and a kinase. Upon exposure to the sample, the composition may become phosphorylated to form a product having increased affinity for $Mg^{2+}$. The phosphorylated product may then bind $Mg^{2+}$, resulting in an enhancement of fluorescence via chelation-enhanced fluorescence (CHEF). The fluorescence of the composition may then be analyzed to determining the presence and/or amount of a phosphorylated product.

Methods described herein may be performed in vitro or in vivo. For in vitro applications, the reaction is typically conducted in a buffer containing $Mg^{2+}$ and a phosphoryl donor. Suitable buffers include, for example, HEPES and TRIS. One possible $Mg^{2+}$ source is $MgCl_2$. One possible phosphoryl donor is ATP. For in vitro applications, the concentration of kinase can range from about 0.5 nM to about 1 micromolar, in some cases not more than about 500 nM, and in some cases not more than about 250 nM. The concentrations of sensor can vary, but is usually ranges between about 0.1 µM to 10 mM. Adenosine 5'-triphosphate (ATP) may be used as the phosphoryl donor, in stock solutions of about 10-100 mM. Saturating concentrations of ATP may be used to arrive at values of $K_m$ and $V_{max}$ for the substrates. For in vivo applications, when the sensor is internalized into a cell, sufficient kinases, $Mg^{2+}$, and phosphate donors exist in the cytosol. For in vivo sensing, a cellular internalization sequence can be included in the sensor design. Suitable cellular internalization sequences include Penetratins, HIV-Tat domains and poly-arginine sequences.

In one set of embodiments, compositions and methods for monitoring and/or imaging species associated with kinase or phosphorylation activity are provided. As used herein, "species associated with kinase or phosphorylation activity" refer to any species that triggers (e.g., catalyzes), initiates, performs, or otherwise promotes the transfer of a phosphate group to and/or from a substrate. The species may be an enzyme, such as a kinase (e.g. mitogen-activated protein kinase-activated protein kinase-2 (MK2), sarcoma kinase (Src), Ser/Thr and Tyr kinases) or a phosphatase, a small molecule (e.g., ATP), an ion (e.g., $Mg^{2+}$), or other species. In some cases, the species may phosphorylate or de-phosphorylate a portion of the compositions described herein. For example, a compound comprising a fluorophore and a protein kinase substrate or at least one amino acid may be exposed to a sample containing a kinase, such that the compound can be recognized by and/or may be phosphorylated by the kinase.

Various kinases may be analyzed using methods described herein. For example, serine/threonine and tyrosine kinases can be used in the present invention. Other exemplary kinases include cAMP dependent protein kinase, protein kinase C, Ca/calmodulin dependent kinases, AMP activated kinase, s6 kinases, eIF-2 kinases, p34.sup.cdc2 protein kinase, mitogen activated protein kinases, casein kinase-2, casein kinase-1, glycogen sythase kinase-3, Tyr-specific protein kinases. For applications in which the kinase is dependent on cofactors, a source of cofactor may also be included in the sample. For example, for PKC, sources of $Ca^{2+}$, phospholipid, and diacylglycerol may be used.

The compositions described herein may also be useful as fluorescence probe molecules in monitoring biological interactions. Biological interactions play important roles in the sequence and mechanisms of action of various cellular processes and signal pathways. Accordingly, the time course, nature, and sequence of the different cellular processes can be elucidated by in situ observation using certain compositions of the present invention. Specific inhibitors and/or activators of the cellular processes and signal pathways may optionally be used in addition to compounds of the present invention.

In some cases, the method may involve exposing a composition as described herein to a target molecule (e.g., a peptide), and determining the fluorescence of the biological sample at various stages during a biological event or interaction. The compound may be a peptide substituted with a composition as described herein. In some cases, the compound may be a peptide containing an amino acid residue that is modified by composition as described herein.

The fluorescence of the compositions may be analyzed or measured using methods known in the art. In some cases, the intensity and/or wavelength of the emitted fluorescent energy may determine the presence or amount of analyte in the same, or may provide other information about the sample. The composition/sample may be exposed to electromagnetic radiation having a wavelength of about 375 nm or greater. In some embodiments, the composition/sample may be exposed to electromagnetic radiation having a wavelength between about 375 nm and about 700 nanometers nm, between about 490 nm and about 700 nanometers nm, between about 520 nm and about 700 nm, or between about 500 nm and about 600 nm, among other ranges.

In some cases, the fluorescence of a molecule may be defined by the quantum yield. The quantum yield is the ratio of the photons absorbed by the compound to the photons emitted through fluorescence by the compound. Compounds of the present invention have quantum yields that may be relatively low in aqueous solutions, but higher in non-polar environments. Quantum yields for various embodiments may range from about 0.001 and about 0.8, or between about 0.001 and about 0.005 for non-chelated compounds, or between about 0.1 and about 0.8 for chelated compounds. The fluorescence can also be evaluated by determining the dipole moment change between the ground and excited state. The change in the dipole moment can be estimated from a plot of the Stokes shift vs. the orientation polarizability, known as a Lippert-Mataga plot, known to those of ordinary skill in the art. As fluorescence can be sensitive to the pH of the surrounding environment, certain compositions of the present invention are useful as fluorescence probes or sensors in the pH range from about 4 to about 8.

The concentration of the composition used may depend on external factors such as the detection equipment. Typically, the concentration of the composition in the sample is from greater than about 0.1 nM. A sensor of various embodiments of the present invention can be used in a method for detecting biological interactions. The methods of certain embodiments of the present invention include providing a peptide incorporating an amino acid comprising a compound of formula (I), (II), or (III), contacting a target molecule with the peptide to form a biological sample, and monitoring the fluorescence of the biological sample.

As described herein, some embodiments of the invention provide proteins or peptides substituted with compounds as described herein, where the compound may be attached to the peptides either during or after peptide synthesis. In some embodiments, the peptide may be first synthesized with protecting groups on the side chains of the peptide. Upon selective removal of certain protecting groups, the compound can be coupled to the side chains of the peptides using standard coupling methods. For example, when (I), (II), or (III) comprise a halo alkyl group (i.e., bromomethyl), the compound can be coupled to a residue containing a thiol group in its side chain (such as Cys) forming a thioether linkage. In another example, when (I), (II), or (III) comprise an amine, the amine can be coupled to a residue containing a carboxylic acid in its side chain (such as Asp or Glu), forming an amide linkage. Also, when (I), (II), or (III) comprise a thiol, the thiol can be coupled to a residue containing a thiol group in its side chain (such as Cys), forming a disulfide linkage. In another embodiment, when (I), (II), or (III) comprise a carboxylic acid, the carboxylic acid can be coupled to a residue containing an amine in its side chain. In another example, when (I), (II), or (III) comprise an aldehyde, it can be coupled to a residue containing an amine via reductive amination. The fluorophore-containing peptide may then be deprotected and purified in some cases.

In some embodiments, a triazole structure may be incorporated into a compound after the compound is coupled to a peptide. For example, the compound may comprise an azido group that can be reacted with an alkyne to form a triazole after the compound is coupled to a peptide. Such an approach may be advantageous, for example, for creating a library of modified peptides, with each peptide containing a compound that has been reacted with a different alkyne.

Selective deprotection of amino acids is well known in the art. One method is to use orthogonal side-chain protection such as allyl (OAll) (for the carboxyl group in the side chain of glutamic acid or aspartic acid, for example), allyloxy carbonyl (Alloc) (for the amino nitrogen in the side chain of lysine or ornithine, for example), p-methoxytrityl (MMT) or acetamidomethyl (Acm) (for the sulfhydryl of cysteine). OAll and Alloc are easily removed by Pd, Acm can be removed by iodine treatment, and MMT can be removed by mild acid treatment.

Methods for introduction and removal of N-protecting groups are known to those skilled in the art, examples of which are disclosed in Greene and Wuts, Protective Groups in Organic Synthesis, 2nd ed.; John Wiley & Sons, New York, 1991.

As a non-limiting example, a peptide may be reacted with a compound of formula (IV):

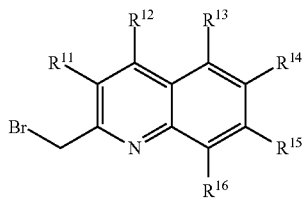

Such a reaction may produce, in some embodiments, peptides having an amino acid residue of formula (V):

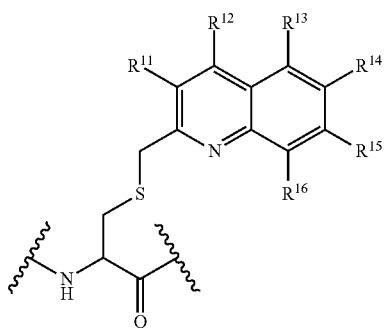

The peptide to be modified may be any suitable peptide, for example, naturally occurring, artificial or synthetically produced, etc. As a specific example, a peptide may be a peptide that comprises a target recognition sequence, such as an SH2-domain recognition sequence. Examples of SH2-domain recognition sequences include, but are not limited to, pTyr-Asp-His-Pro or pTyr-Glu-Asn-Val.

Examples of synthesis techniques are discussed in the examples, below, and those of ordinary skill in the art will be able to readily modify such techniques as needed in order to reach a particular structure without an undue amount of experimentation. In some cases, a composition of the invention is synthesized using a commercially-available anhydride as a starting material. In some cases, various protecting groups may be utilized in the synthesis of the compositions. The phrase "protecting group" as used herein refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Any of the compositions described herein may be substituted with one or more protecting groups.

DEFINITIONS

For convenience, certain terms employed in the specification, examples, and appended claims are listed here.

The term "hydroxy" is given its ordinary meaning in the art and refers to an —OH group.

The term "amino" is given its ordinary meaning in the art and refers to a —NR'R" group, where R' and R" are each independently hydrogen or alkyl.

The term "thiol" is given its ordinary meaning in the art and refers to a —SR' group, where R' is hydrogen.

The term "halogen" or "halo" is given its ordinary meaning in the art and refers to a chlorine, bromine, iodine, or fluorine atom.

The term "alkyl" means a hydrocarbon group that may be linear, cyclic, or branched or a combination thereof having the number of carbon atoms designated (i.e., C1-8 means one to eight carbon atoms). An alkyl group may be saturated or unsaturated. Unsaturated alkyl groups may be conjugated, partially conjugated, or unconjugated. "Conjugated" as used herein in the context of unsaturated groups has its ordinary meaning as known in the art. Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl groups include haloalkyl, thioalkyl, aminoalkyl, and the like.

The term "aryl" means a polyunsaturated, aromatic hydrocarbon group having a single ring (monocyclic) or multiple rings (bicyclic or polycyclic), which can be fused together or linked covalently. Examples of aryl groups include phenyl and naphthalene-1-yl, naphthalene-2-yl, biphenyl and the like. Aryl groups can be substituted or unsubstituted, unless otherwise indicated.

The term "azido" is given its ordinary meaning in the art and refers to an —N₃ group.

The term "heteroaryl" means an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

The term "heterocyclyl" or "heterocyclic," which are synonymous as used herein, means a saturated or unsaturated ring containing at least one heteroatom (typically 1 to 5 heteroatoms) selected from nitrogen, oxygen or sulfur. The heterocyclyl ring may be monocyclic or bicyclic. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like.

The term "ring" means a compound whose atoms are arranged in formulas in a cyclic form. The ring compound can be either carbocyclic or heterocyclic.

The term "carbocyclic" means a ring composed exclusively of carbon atoms.

The term "substituent" means an atom or a group that replaces another atom or group in a molecule.

The terms "N-terminal protecting group" or "N-protecting group" refer to a group that prevents undesirable reaction of the amino functional group during subsequent transformations. The use of N-protecting groups is well known in the art for protecting groups against undesirable reactions during a synthetic procedure and many such protecting groups are known. Commonly used N-protecting groups are known to those skilled in the art, examples of which are disclosed in Greene and Wuts, Protective Groups in Organic Synthesis, 2nd ed.; John Wiley & Sons, New York, 1991). Examples of N-protecting groups include, but are not limited to, benzyl, substituted benzyl, benzyloxycarbonyl (Cbz), tert-butoxycarbonyl (Boc), 9-fluorenylmethoxycarbonyl (Fmoc), trityl, N-veratyloxycarbonyl (N-Voc), N-allyloxycarbonyl (N-Alloc) and N-pentenoyl (N-Pent), acyl groups including formyl, acetyl (Ac), trifluoroacetyl, trichloroacetyl, propionyl, pivaloyl, t-butylacetyl, acylisothiocyanate, aminocaproyl, benzoyl and the like; acyloxy groups, including t-butyloxycarbonyl (Boc), benzyloxycarbonyl (Cbz), 9-fluorenylmethoxycarbonyl (Fmoc), p-methoxybenzyloxycarbonyl, methoxycarbonyl, ethoxycarbonyl, allyloxycarbonyl and the like; sulfonyl groups such as benzenesulfonyl, p-toluenesulfonyl and the like; arylalkyl groups such as benzyl, triphenylmethyl, benzyloxymethyl and the like; and silyl groups such as trimethylsilyl, t-butyldimethylsilyl and the like.

The term "C-terminal protecting group" refers to a group that prevents undesirable reaction of the carboxyl functional group and includes, but is not limited to, $C_1$-$C_{12}$ alkyl (e.g., tert-butyl) and $C_1$-$C_{12}$ haloalkyl.

The term "chelation-enhanced fluorescence (CHEF)" means fluorescence enhancement of a compound as a result of metal ion binding (chelation) to that compound.

The term "capping group" means a chemical group connected to the N- or C-terminus of a peptide to prevent the peptide from degrading.

"Alkoxy" refers to —O-alkyl. Examples of an alkoxy group include methoxy, ethoxy, n-propoxy, etc.

"Haloalkyl," as a substituted alkyl group, refers to a mono-haloalkyl or polyhaloalkyl group, most typically substituted with from 1-3 halogen atoms. Examples include 1-chloroethyl, 3-bromopropyl, trifluoromethyl and the like.

All of the above terms (e.g., "alkyl," "aryl," "heteroaryl" etc.), in some embodiments, include both substituted and unsubstituted forms of the indicated groups. These groups may be substituted multiple times, as chemically allowed. Suitable substituents include alkyl, aryl, heteroaryl, heterocyclyl, halogen, alkoxy, oxygen, and nitrogen.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Fluorescence" encompasses the release of fluorescent energy. Less broadly, the term "fluorescence" refers to fluorescent emission, the rate of change of fluorescence over time (i.e., fluorescence lifetime), fluorescence polarization, fluorescence anisotropy, and fluorescence resonance energy transfer. See Eftink, M. R., Biophysical J. 66:482-501 (1994).

"Fluorescence probe molecule" refers to a compound of the present invention. The compound, after excitement by light of a defined wavelength or defined range of wavelengths, is capable of emitting fluorescent energy. The fluorescent molecule or a compound may be capable of binding to a peptide, protein, membrane or receptor.

The term "biological interactions" encompasses the interaction of a compound or molecule with a target molecule.

"Protein" and "peptide," as used herein, are synonymous. The peptide may comprise any number of amino acids. For instance, the peptide of the present invention may comprise 2-100 amino acids, 2-30 amino acids, 2-20 amino acids, or 3-10 amino acids. For proteins or peptides, the term "unfolding" encompasses any change in structure due to heating. For example, the term "unfolding" refers to the transition of from the liquid crystalline state to the molten globule state. In the molten globule state, tertiary and quaternary structure has been altered, relative to the native state of the protein, and at least some secondary structure remains intact. The term "unfolding" also encompasses loss of crystalline ordering of amino acid side-chains, secondary, tertiary or quaternary structure. The term "unfolding" also encompasses formation of a random coil.

"Folding" and "refolding," and "renaturing" refer to the acquisition of the correct amino acid side-chain ordering, secondary, tertiary, or quaternary structure, of a protein or a nucleic acid, which affords the full chemical and biological function of the biomolecule.

The term "target molecule" encompasses peptides, proteins, nucleic acids, ions, and other receptors. The term encompasses both enzymes, and proteins which are not enzymes. The term encompasses monomeric and multimeric proteins. Multimeric proteins may be homomeric or heteromeric. The term encompasses nucleic acids comprising at least two nucleotides, such as oligonucleotides. Nucleic acids can be single-stranded, double-stranded, or triple-stranded. The term encompasses a nucleic acid which is a synthetic oligonucleotide, a portion of a recombinant DNA molecule, or a portion of chromosomal DNA. The term target molecule also encompasses portions of peptides, proteins, and other receptors which are capable of acquiring secondary, tertiary, or quaternary structure through folding, coiling or twisting. The target molecule may be substituted with substituents including, but not limited to, cofactors, coenzymes, prosthetic groups, lipids, oligosaccharides, or phosphate groups.

The terms "target molecule" and "receptor" are synonymous. Examples of target molecules are included, but not limited to those disclosed in Faisst, S. et al., Nucleic Acids Research 20:3-26 (1992); Pimentel, E., Handbook of Growth Factors, Volumes I-III, CRC Press, (1994); Gilman, A. G. et al., The Pharmacological Basis of Therapeutics, Pergamon Press (1990); Lewin, B., Genes V, Oxford University Press (1994); Roitt, I., Essential Immunology, Blackwell Scientific Publ. (1994); Shimizu, Y., Lymphocyte Adhesion Molecules, R G Landes (1993); Hyams, J. S. et al., Microtubules, Wiley-Liss (1995); Montreuil, J. et al., Glycoproteins, Elsevier (1995); Woolley, P., Lipases: Their Structure Biochemistry and Applications, Cambridge University Press (1994); Kurjan, J., Signal Transduction: Prokaryotic and Simple Eukaryotic Systems, Academic Press (1993); Kreis, T., et al., Guide Book to the Extra Cellular Matrix and Adhesion Proteins, Oxford University Press (1993); Schlesinger, M. J., Lipid Modifications of Proteins, CRC Press (1992); Conn, P. M., Receptors: Model Systems and Specific Receptors, Oxford University Press (1993); Lauffenberger, D. A. et al, Receptors. Models For Binding Trafficking and Signaling, Oxford University Press (1993); Webb, E. C., Enzyme Nomenclature, Academic Press (1992); Parker, M. G., Nuclear Hormone Receptors; Molecular Mechanisms, Cellular Functions Clinical Abnormalities, Academic Press Ltd. (1991); Woodgett, J. R., Protein Kinases, Oxford University Press (1995); Balch, W. E. et al., Methods in Enzymology, Vol. 257, Pt. C: "Small GTPases and Their Regulators: Proteins Involved in Transport," Academic Press (1995); The Chaperonins, Academic Press (1996); Pelech, L., Protein Kinase Circuitry in Cell Cycle Control, R G Landes (1996); Atkinson, Regulatory Proteins of the Complement System, Franklin Press (1992); Cooke, D. T. et al., Transport and Receptor Proteins of Plant Membranes: Molecular Structure and Function, Plenum Press (1992); Schumaker, V. N., Advances in Protein Chemistry: Lipoproteins, Apolipoproteins, and Lipases, Academic Press (1994); Brann, M., Molecular Biology of G-Protein-Coupled Receptors: Applications of Molecular Genetics to Pharmacology, Birkhauser (1992); Konig, W., Peptide and Protein Hormones: Structure, Regulations, Activity—A Reference Manual, VCH Publ. (1992); Tuboi, S. et al., Post-Translational Modification of Proteins, CRC Press (1992); Heilmeyer, L. M., Cellular Regulation by Protein Phosphorylation, Springer-Verlag (1991); Takada, Y., Integrin: The Biological Problem, CRC Press (1994); Ludlow, J. W., Tumor Suppressors: Involvement in Human Disease, Viral Protein Interactions, and Growth Regulation, R G Landes (1994); Schlesinger, M. J., Lipid Modification of Proteins, CRC Press (1992); Nitsch, R. M., Alzheimer's Disease. Amyloid Precursor Proteins, Signal Transduction, and Neuronal Transplantation, New York Academy of Sciences (1993); Cochrane, C. G., et al., Cellular and Molecular Mechanisms of Inflammation, Vol. 3: Signal Transduction in Inflammatory Cells, Part A, Academic Press (1992); Gupta, S. et al., Mechanisms of Lymphocyte Activation and Immune Regulation IV: Cellular Communications, Plenum Press (1992); Authi, K. S. et al., Mechanisms of Platelet Activation and Control, Plenum Press (1994); Grunicke, H., Signal Transduction Mechanisms in Cancer, R G Landes (1995); and Latchman, D. S., Eukaryotic Transcription Factors, Academic Press (1995), all of which are incorporated herein by reference in their entirety.

The term "contacting a target molecule" refers broadly to placing the target molecule in solution with the molecule to be screened for binding or with the condition(s) to be tested for stabilizing the target molecule. Less broadly, contacting refers to the turning, swirling, shaking or vibrating of a solution of the target molecule and the molecule to be screened for binding. More specifically, contacting refers to the mixing of the target molecule with the molecule to be tested for binding. Mixing can be accomplished, for example, by repeated uptake and discharge through a pipette tip, either manually or using an automated pipetting device. Contacting can refer to the equilibration of binding between the target molecule and the molecule to be tested for binding. Contacting can occur in the container, infra, or before the target molecule and the molecule to be screened are placed in the container.

The target molecule may be contacted with a nucleic acid prior to being contacted with the molecule to be screened for binding. The target molecule may be complexed with a peptide prior to being contacted with the molecule to be screened for binding. The target molecule may be phosphorylated or dephosphorylated prior to being contacted with the molecule to be screened for binding.

A carbohydrate moiety may be added to the target molecule before the target molecule is contacted with the molecule to be screened for binding. Alternatively, a carbohydrate moiety may be removed from the target molecule before the target molecule is contacted with the molecule to be screened for binding.

The term "container" refers to any vessel or chamber in which the receptor and molecule to be tested for binding can be placed. The term "container" encompasses reaction tubes (e.g., test tubes, microtubes, vials, etc.).

"Spectral emission," "thermal change," and "physical change" encompass the release of energy in the form of light or heat, the absorption of energy in the form or light or heat, changes in turbidity and changes in the polar properties of light. Specifically, the terms refer to fluorescent emission, fluorescent energy transfer, absorption of ultraviolet or visible light, changes in the polarization properties of light, changes in the polarization properties of fluorescent emission, changes in the rate of change of fluorescence over time (i.e., fluorescence lifetime), changes in fluorescence anisotropy, changes in fluorescence resonance energy transfer, changes in turbidity, and changes in enzyme activity. The terms may refer to fluorescence, including to fluorescence emission. Fluorescence emission can be intrinsic to a protein or can be due to a fluorescence reporter molecule. The use of fluorescence techniques to monitor protein unfolding is well known to those of ordinary skill in the art. For example, see Eftink, M. R., Biophysical J. 66:482-501 (1994).

"Biochemical conditions" encompass any component of a physical, chemical, or biochemical reaction. Specifically, the term refers to conditions of temperature, pressure, protein concentration, pH, ionic strength, salt concentration, time, electric current, potential difference, concentrations of cofactor, coenzyme, oxidizing agents, reducing agents, detergents, metal ion, ligands, or glycerol.

As used herein, the term "determining" generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction.

U.S. Provisional Patent Application Ser. No. 61/238,601, filed Aug. 31, 2009, entitled "Kinase Sensors," by Imperiali et al., is incorporated herein by reference.

The following examples are intended to illustrate certain embodiments of the present invention, but do not exemplify the full scope of the invention.

EXAMPLES

Example 1

This example describes the synthesis and screening of Oxn derivatives. A selection of substituted hydroxyquinoline derivatives related to a sulfonamide derivative (FIG. 1, complex 1), but bearing different acceptor groups at position 5 (FIG. 1, complexes 2-7) was prepared using previously described methods. These analogs were screened for fluorescence in the presence of excess $Mg^{2+}$ and under buffered aqueous conditions. FIG. 1 lists fluorescence data for compounds 1-7. Spectra were acquired in 150 mM NaCl, 50 mM HEPES (pH 7.4), 25° C. with 10 μM 1-7 and 10 mM $MgCl_2$. Excitation of all species is provided at $\lambda_{max}$ (355-425 nM). Quantum yields were calculated with reference to a quinine sulphate standard (in 0.05 M $H_2SO_4$. Complex 1 has $\epsilon_{355}=8,247$ $cm^{-1}M^{-1}$. Notably, the excitation and emission wavelengths were similar to those of 1; however, the quantum yields are poorer. Indeed, only the aldehyde-substituted chromophore 2 showed an improved quantum yield. This derivative exhibited shorter $\lambda_{em}$, and the aldehyde group was readily oxidized.

Figure 2:
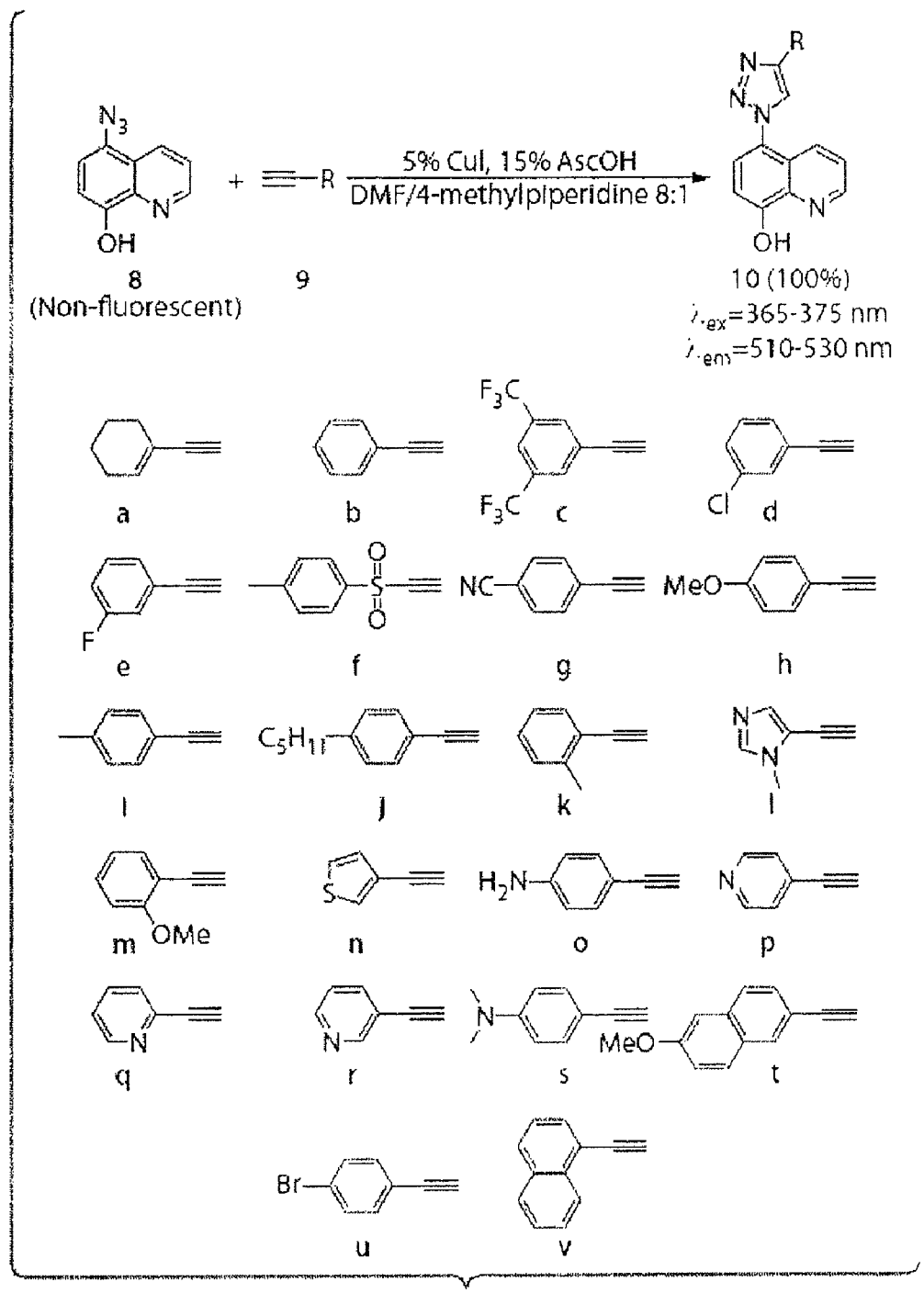
FIG. 2 shows the synthesis of various compositions described herein via a 1,3-dipolar cycloaddition reaction.

Azide 8 (FIG. 2) was prepared using previously reported methods. Azide 8 showed low or essentially no fluorescence, and, without wishing to be bound by theory, this effect may be attributed to the quenching effect from the electron-rich azido group. In the presence of catalytic Cu(I) and ascorbic acid, 8 reacted readily at room temperature with 1-ethynylcyclohexene (9a) in DMF/4-methylpiperidine (8:2) to afford the cycloaddition product 10a in essentially quantitative yield. Quinoline 10a had a $\lambda_{ex}$ of 371 nm and a $\lambda_{em}$ of 522 nm. The fluorescence properties of the triazole-substituted quinolines were investigated for the products from the 1,3-dipolar cycloaddition reaction of 8 with 21 additional alkynes (9b-v) (FIG. 2).

The cycloaddition reactions were generally complete in 12 h at room temperature and were monitored by TLC and mass spectrometry. The formation of the fluorescent triazole compounds could be easily established upon exposure to a hand-held UV lamp ($\lambda_{ex}$=365 nm).

Figure 3:
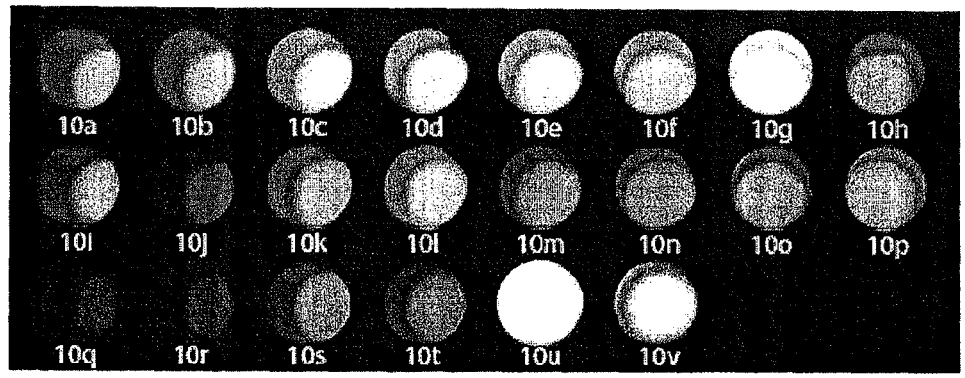
FIG. 3 shows qualitative comparison of emission wavelengths of various compositions.

The fluorophores were then qualitatively compared in a 96-well plate (transilluminator; $\lambda_{ex}$=365 nm) to identify promising compounds (FIG. 3) and were further subjected to quantitative analysis in a fluorescence plate reader (FIG. 8). In FIG. 8, the quantum yields of selected fluorophores were calculated with reference to quinine sulphate (in 0.05 M $H_2SO_4$) as a standard (vide infra). Compound 10u has $\epsilon_{355}$=7905 $cm^{-1}M^{-1}$ (vide infra). The excitation and emission wavelengths of the triazole products (10b-v, $\lambda_{ex}$=360-375 nm, $\lambda_{em}$=510-530 nm) were improved compared to those for Sox (1, $\lambda_{ex}$=360 nm, $\lambda_{em}$=485 nm, Φ=0.342, $\epsilon_{355}$=8,247 $cm^{-1}M^{-1}$). Based on the preliminary screening, selected targets were then synthesized in larger quantities and the quantum yields of the corresponding hydroxyquinoline derivatives were determined. Compared to 10a (Φ=0.033) a 3.5-fold improvement in quantum yield was obtained in the case of the bromide 10u ($\lambda_{ex}$=375 nm, $\lambda_{em}$=525 nm, Φ=0.111, $\epsilon_{355}$=7,905 $cm^{-1}M^{-1}$). In view of the fluorescent properties of this derivative, it was chosen for use as a chelation-sensitive fluorophore to prepare probes for mitogen-activated protein kinase-activated protein kinase-2 (MK2), and sarcoma kinase (Src), used as models of Ser/Thr and Tyr kinases, respectively. For the purposes of comparison, the analogous fluorescent peptides containing the original Sox chromophore were also prepared as previously described.

Example 2

Figure 4:
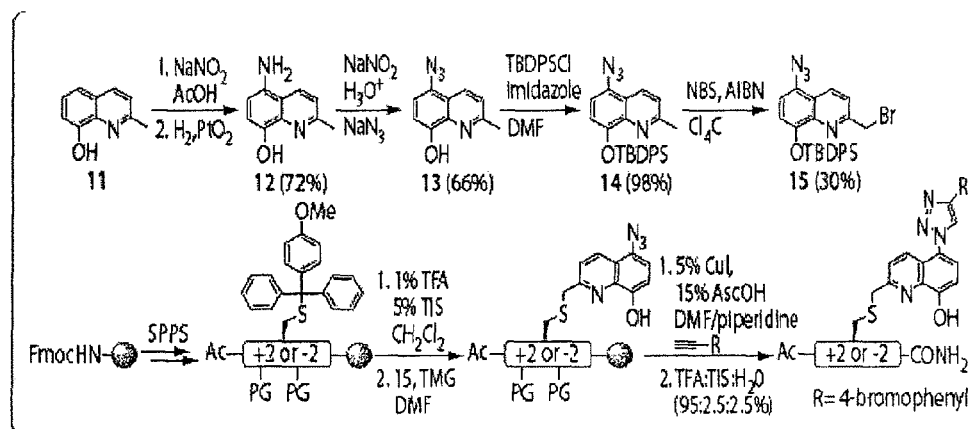
FIG. 4 shows the synthesis of a protein kinase sensor, according to one embodiment of the invention.

This example demonstrates the synthesis and evaluation of Clk-based peptidyl kinase substrates. The synthesis of the probes is outlined in FIG. 4. Diazotization of 5-amino-2-methylquinolin-8-ol (12, prepared from 8-hydroxyquinaldine using previously described methods) followed by treatment of the diazonium salt with $NaN_3$ gave the corresponding azide 13 (66% yield). Protection of the phenolic hydroxyl group as a tert-butyldiphenylsilyl ether produced 14 (98% yield), which was then brominated under free radical conditions to afford the bromide 15 (30% yield). To avoid dibromination, the reaction was stopped after 20 min, thereby providing a mixture of the desired product (15) and the starting material (14), which was not separated and was used in the next step without purification. Fmoc-based solid phase peptide synthesis (SPPS) was utilized to assemble the intact peptide that included an appropriately placed cysteine residue protected with monomethoxytrityl (Mmt), which is an acid-labile protecting group (FIG. 4). After selective on-resin sulfhydryl deprotection, the free thiol was alkylated with 15. Then a 1,3-dipolar cycloaddition reaction with 1-bromo-4-ethynylbenzene in the presence of catalytic Cu(I) gave the corresponding triazole-substituted peptide. Standard TFA cleavage from the resin and concomitant removal of all side-chain protecting groups revealed the desired chemosensor (>95% yield).

FIG. 5 shows the substrate sequences of the Sox- and click (Clk)-based RDF probes for MK2 and Src kinases, as well as the fluorescence increases that were observed with the corresponding phosphopeptides. The difference in fluorescence was determined by comparison of the fluorescence intensity at the maximum emission wavelength (485 nm for Sox and 525 nm for Clk) of phosphorylated and unphosphorylated peptides in the presence of $Mg^{2+}$. The location of the chromophore was determined in reference to the chromophore, where C denotes C-terminus and N stands for N-terminus. The asterisk (*) denotes the residue that is phosphorylated. In cases where it has been determined, residues important in kinase recognition are underlined. The Fold Fluorescence Increase was measured in triplicate as a quotient of fluorescence intensity at 485 nm (for Sox peptides) or 525 nm (for Clk peptides) of phosphopeptide and substrate in 20 mM HEPES (pH 7.4), 10 mM $MgCl_2$ and 10 μM peptide (for Sox peptides $\lambda_{ex}$=360 nm; for Clk peptides $\lambda_{ex}$=375 nm). The fluorescence increases of the click peptides are between 2- and 2.5-fold. The click-based RDF peptides exhibited larger fluorescence increases than the Sox-based RDF peptides in the case of Src (FIG. 5, entries 3 and 4) while this trend is reversed in the case of MK2 (FIG. 5, entries 1 and 2). As an example, FIG. 6A shows a comparison between the fluorescence excitation and emission spectra of the synthetically-obtained phosphopeptide MK2(Sox) [P1 (--)] and that from the analogous MK2(Clk) [P2(-)]. Samples were prepared in 50 mM HEPES (pH 7.4) and 150 mM NaCl. Spectra were acquired at 25° C. and were baseline-corrected using a sample of the buffer solution. In the case of the Src sensors the result was the same. Neither species was fluorescent at pH 7.0 (50 mM HEPES, 150 mM NaCl) in the absence of the metal ion. Upon addition of $Mg^{2+}$ the fluorescence spectra of Mg2+-bound P1 and Mg2+-bound P2 exhibited emission maxima of 485 and 525 nm, respectively, indicating a red-shift of 40 nm. On the other hand, in the corresponding excitation spectra the $Mg^{2+}$-bound P1 reached a maximum at 360 nm and $Mg^{2+}$-bound P2 emission peaked at 375 nm, representing a bathochromic shift of 15 nm.

Example 3

This example demonstrates evaluation of Clk-based substrates in enzymatic assays. Following established protocols, Sox- and Clk-based substrates (FIG. 5, entries 1 and 2, respectively) were subjected to MK2 under identical conditions and then the overall turnover of each substrate was compared. FIG. 6B shows the percentage of turnover of the Clk-based (■, FIG. 5, entry 2) or Sox-based (□, FIG. 5, entry 1) substrate with MK2 after 10 min. Assays were performed in 20 mM HEPES (pH 7.4), 10 mM MgCl2, 0.1 mM EGTA, 0.01% Brij 35, 0.1 mg/mL BSA, 1 mM DTT, 1 mM ATP, 5 µM substrate and 10 ng MK2 at 30° C. Plotted values indicate the mean±s.e.m. for triplicate measurements. As shown in FIG. 6B, MK2 phosphorylated the Clk-substrate just as efficiently as the Sox substrate indicating that the size of Clk chromophore does not adversely influence reaction kinetics.

In conclusion, the synthesis, peptide incorporation, and characterization of new phosphorylation chemosensors that contain 1,3-triazole-substituted 8-hydroxyquinolines and exhibit improved fluorescence properties compared to Sox was achieved. This modification results in significant red-shifts in the excitation (15 nm) and emission maxima (40 nm) of the chromophore when complexed to $Mg^{2+}$. Moreover, the chromophore does not inhibit the ability of MK2 to recognize and phosphorylate the Clk probe.

Example 4

This example provides the materials and methods information for Example 1-3 above.

General information. All solvents and reagents were obtained commercially and used without further purification, unless otherwise noted. Nα-Fmoc-protected amino acids [Fmoc-Ala-OH, Fmoc-Arg(Pbf)-OH, Fmoc-Cyc(Mmt)-OH, Fmoc-Glu(OtBu)-OH, Fmoc-Gln(Trt)-OH, Fmoc-His(Trt)-OH, Fmoc-Ile-OH, Fmoc-Leu-OH, Fmoc-Lys(Boc)-OH, Fmoc-Phe-OH, Fmoc-Ser(tBu)-OH, Fmoc-Ser(PO(OBn) OH)-OH, Fmoc-Tyr(tBu)-OH, Fmoc-Tyr(PO(OBn)OH)-OH]§ were purchased from Novabiochem. Whenever anhydrous and/or degassed CH2Cl2 was necessary it was distilled from calcium hydride under an argon atmosphere. Analytical TLC was performed on silica gel 60 $F_{254}$ precoated plates (EMD Chemicals Inc.) and visualized by UV. Flash column chromatography was performed as previously described using forced flow of the indicated solvent on AdTech Flash Silica Gel (32-60 micron packing, 60 Angstrom pore diameter, Adedge Technologies). Organic solutions were concentrated in vacuo by rotary evaporation at ~10 Torr (house vacuum) at 25-40° C., then at ~0.5 Torr (vacuum pump), unless otherwise indicated. Peptides were purified via preparative reverse-phase C18 HPLC employing a gradient of solvents A ($H_2O$ with 0.1% v/v TFA) and B ($CH_3CN$ with 0.1% v/v TFA). Compounds were characterized by $^1H$, $^{13}C$ NMR and mass spectrometry. Peptide purity was determined by analytical reverse-phase HPLC.

Abbreviations. AIBN: Azobisisobutyronitrile; ATP: adenosine triphosphate; Bn: benzyl; tBu: t-butyl; Boc: tbutoxycarbonyl; DIEA: diisopropylethylamine; BSA: bovine serum albumin; DMF: N,N-dimethylformamide; DMSO: dimethyl sulfoxide; DTT: dithiothreitol; EDTA: ethylenediaminetetraacetic acid; EGTA: glycol-bis(2-aminoethylether)-N,N,N',N'-tetraacetic acid; ESI-MS: Electrospray Ionization Mass Spectrometry; Fmoc: 9-fluorenylmethoxycarbonyl; FPR: fluorescence plate reader; HEPES: 4-(2-hydroxyethyl)-1-piperazine ethane sulfonic acid; HOAt: 7-aza-1-hydroxybenzotriazole; HOBt: 1-hydroxybenzotriazole; HPLC: high performance liquid chromatography; HRMS: high resolution mass spectrometry; MK2: mitogen-activated protein kinase-activated protein kinase-2; Mmt: 4-methoxytrityl; NBS: N-bromosuccinimide; NMR: nuclear magentic resonance; Pbf: 2,2,4,6,7-pentamethyldihydrobenzofuran-5-sulfonyl; PyAOP: (7-azabenzotriazol-1-yloxy)tripyrrolidinophosphonium hexafluorophosphate; PyBOP: Benzotriazol-1-yl-oxytripyrrolidinophosphonium hexafluorophosphate; RDF: recognition-domain focused; Sox-Br: 2-bromomethyl-8-t-butyldiphenylsilyloxy-5-(N,Ndimethyl)sulfonamidoquinoline; SPPS: solid-phase peptide synthesis; Src: sarcoma kinase; TFA: trifluoroacetic acid; TIS: triisopropylsilane; TLC: thin-layer chromatography; TNBS: 2,4,6-trinitrobenzene sulfonic acid; Trt: trityl; UV: Ultra-Violet.

Instrumentation. NMR: $^1H$ and $^{13}C$ NMR spectra were recorded on a Bruker 400 MHz Avance spectrometer. Chemical shifts (δ) are reported in parts per million (ppm) and referenced to $CDCl_3$ (7.26 ppm for $^1H$ and 77.0 ppm for $^{13}C$). Coupling constants (J) are reported in Hertz (Hz) and multiplicities are abbreviated as singlet (s), doublet (d), doublet of doublets (dd), triplet (t) and multiplet (m). HPLC: HPLC was carried out on Waters Prep LC 4000 System or Waters Delta 600 System equipped with Waters 2487 dual wavelength absorbance detectors. Columns used: C18 analytical (flow rate=1 mL/min), Beckman Ultrasphere ODS, 5 micron, 150× 4.6 mm; C18 preparatory (flow rate=15 mL/min), YMC-Pack Pro, 5 micron, 250×2 20 mm. ESI-MS: Applied Biosystems Mariner mass spectrometer. MALDI-TOF MS: PerSeptive Biosystems Voyager MALDI-TOF instrument. HRMS: Provided by the Department of Chemistry Instrumentation Facility (DCIF), MIT. UV-Vis Spectrophotometer: Shimadzu UV-2401PC. Fluorometer: Fluoromax 3 from Jobin Yvon. Cuvette: Starna Cells (16.100E-Q-10) 100 microliter sub-micro cuvette, 1 cm path length. Fluorescence Plate Reader: HTS 7000 Bio Assay Reader from Perkin Elmer or SpectraMax GeminiXS Dual Scanning Microplate Spectrofluorometer from Molecular Devices. Plate: Corning assay plate, 96-well, half area, no lid, flat bottom, non-binding surface, nonsterile, white polystyrene.

Synthesis of the Triazolyl Derivatives 10a-v. 5-Azido-8-hydroxy-2-methylquinoline (13, 50 mg, 0.26 mmol) and the corresponding alkyne (9a-v) (0.26 mmol) were suspended in a 8:2 mixture of DMF/4-methylpiperidine (2 mL). Ascorbic acid (7.1 mg, 0.04 mmol) and copper iodide (2.5 mg, 0.01 mmol) were added suspended in a 8:2 mixture of dimethylformamide/4-methylpiperidine (1 mL) and the heterogeneous mixture was stirred vigorously overnight in the dark at room temperature. TLC analysis indicated complete consumption of the reactants in 12 h. The mixture was dissolved in ethyl acetate (40 mL), was washed with $H_2O$ (5 mL), brine (5 mL), dried over $Na_2SO_4$, and evaporated to yield the corresponding triazolyl derivatives 10a-v.

Peptide Synthesis. All peptides were synthesized using the standard Fmoc-based amino acid protection chemistry. Peptides were synthesized on Fmoc-PAL-PEG-PS resin (Applied Biosystems, 0.19 mmol/g) using on resin alkylation. The resin was swelled in CH$_2$Cl$_2$ (5 min.) and then DMF (5 min) prior to synthesis. All the amino acids were coupled according to the following procedure: Fmoc deprotection (20% 4-methylpiperidine in DMF, 3×5 min), rinsing step (DMF, 5×), coupling step (amino acid/PyBOP/HOBt/DIEA, 6:6:6:6, 0.15 M in DMF, 30-45 min), rinsing step (DMF, 5×; CH$_2$Cl$_2$, 5×). The coupling was repeated if necessary as determined by the TNBS test. At the end of the synthesis, the Fmoc group was removed with 20% 4-methylpiperidine in DMF (3×5 min.) and the resin was rinsed with DMF (5×). The resin-attached free amines were capped by exposure to Ac$_2$O (20 equiv.) and pyridine (20 equiv.) in DMF for 30 min. The resin was rinsed with DMF (5×), CH$_2$Cl$_2$ (5×) and subjected to 20% 4-methylpiperidine in DMF (3×5 min.). The resin was finally washed with DMF, CH$_2$Cl$_2$, MeOH (5× each) and dried under vacuum.

On-resin Alkylation of Peptides with 15. Resin-attached peptides (50 mg, 0.0095 mmol, 1 equiv.) incorporating Cys (Mmt) were swelled in CH$_2$Cl$_2$, then DMF. The Mmt protecting group was removed from the resin-bound peptide by bubbling N$_2$ through a solution of 1% TFA, 5% TIS in CH$_2$Cl$_2$ (4×20 min). The resin was washed with CH$_2$Cl$_2$ (5×) and DMF (5×). Anhydrous DMF (200 microliters) was added to the resin followed by freshly distilled tetramethylguanidine (5.96 µL, 0.0475 mmol, 5 equiv.). The mixture was incubated for 2-3 min. 15 (17 mg, 0.0285 mmol, 3 equiv.) was dissolved in anhydrous DMF (150 microliters) and added to the resin. After ca. 12 hours of reaction time, the excess reagents were drained and the resin washed with DMF, CH$_2$Cl$_2$, MeOH, CH$_2$Cl$_2$ (5×).

On-resin Click Chemistry of Peptides with 9u. Resin-attached peptides (50 mg, 0.0095 mmol, 1 equiv.) incorporating 5-Azido-8-Hydroxyquinoline were swelled in CH$_2$Cl$_2$, then DMF (5 min). A mixture of 1-bromo-4-ethynylbenzene (9u; 34.4 mg, 0.19 mmol), ascorbic acid (0.75 mg, 0.0043 mmol) and copper iodide (0.27 mg, 0.0014 mmol) was added to the resin suspended in a 8:2 mixture of DMF/4-methylpiperidine (1.5 mL). After ca. 12 hours of reaction time, the excess reagents were drained and the resin washed with DMF, CH$_2$Cl$_2$, MeOH, CH$_2$Cl$_2$ (5×). The resin cleavage and protecting group removal was achieved by exposing the resin-bound peptides to TFA/H$_2$O/TIS (95:2.5:2.5% v/v). The resulting solution was concentrated under a stream of N$_2$ and precipitated by addition of cold Et$_2$O. The pellet was triturated with cold Et$_2$O, redissolved in water, filtered and lyophilized. The peptides were purified by preparative reverse-phase HPLC using UV detection at 228 nm (amide bond absorption) and 316 nm (8-hydroxyquinoline absorption). Only fractions showing a single peak of correct mass by analytical HPLC were used in further experiments.

Synthesis and Characterization of Oxine derivatives. Compounds 1, 2, 3, 4, 6, and 7 were prepared by previously described methods. Characterization of each compound was consistent with literature.

5-Carbaldehyde-8-Hydroxy-2-methylquinoline (2). Yield: 64%, $^1$H NMR (500 MHz, CDCl$_3$) δ ppm: 2.75 (s, 3H), 7.24 (d, J=8 Hz, 1H), 7.51 (d, J=8 Hz, 1H), 7.90 (d, J=8 Hz, 1H), 9.51 (d, J=8 Hz, 1H), 10.01 (s, 1H). $^{13}$C NMR (125 MHz, CDCl$_3$) δ ppm: 24.6, 108.8, 123.6, 124.6, 125.4, 134.6, 137.4, 139.0, 157.4, 158.0, 191.6. HRMS (ESI): calc'd for C$_{11}$H$_9$NO$_2$ [M+H]+: 188.0706, found: 188.0711.

5-Carbonitrile-8-Hydroxy-2-methylquinoline (3). Yield: 79%, $^1$H NMR (500 MHz, CDCl$_3$) δ ppm: 2.77 (s, 3H), 7.15 (d, J=8.5 Hz, 1H), 7.52 (d, J=8.5 Hz, 1H), 7.83 (d, J=8.5 Hz, 1H), 8.37 (d, J=8.5 Hz, 1H). $^{13}$C NMR (125 MHz, CDCl$_3$) δ ppm: 23.7, 27.6, 106.3, 121.1, 124.5, 125.2, 134.0, 137.6, 157.0, 158.9. HRMS (ESI): calc'd for C$_{11}$H$_8$N$_2$O [M+H]+: 185.0709, found: 185.0704.

1-(8-Hydroxy-2-methylquinolin-5-yl)ethanone (4). Yield: 66%, $^1$H NMR (500 MHz, CDCl$_3$) δ ppm: 2.70 (s, 3H), 2.75 (s, 3H), 7.13 (d, J=8 Hz, 1H), 7.46 (d, J=9 Hz, 1H), 8.10 (d, J=8 Hz, 1H), 9.45 (d, J=9 Hz, 1H). $^{13}$C NMR (125 MHz, CDCl$_3$) δ ppm: 24.5, 28.6, 108.3, 124.5, 125.0, 125.2, 133.0, 136.5, 156.0, 157.2, 199.1. HRMS (ESI): calc'd for C$_{12}$H$_{11}$NO$_2$ [M+H]+: 202.0863, found: 202.0856.

8-Hydroxy-2-methylquinoline-5-Carbonyl chloride (5). Compound 5 was prepared with 2-chloroacetyl chloride following the same procedure used to obtain 4. Yield: 71%, $^1$H NMR (500 MHz, CDCl$_3$) δ ppm: 2.76 (s, 3H), 4.78 (s, 2H), 7.15 (d, J=8 Hz, 1H), 7.51 (d, J=9 Hz, 1H), 8.06 (d, J=8 Hz, 1H), 9.39 (d, J=9 Hz, 1H). $^{13}$C NMR (125 MHz, CDCl$_3$) δ ppm 24.6, 46.9, 108.3, 121.3, 125.4, 125.5, 132.7, 135.9, 157.0, 157.7, 191.4. HRMS (ESI): calc'd for C$_{12}$H$_{10}$ClNO$_2$ [M+H]+: 236.0473, found: 236.0479.

8-Hydroxy-5-(4-cyclohexenyl-1H-1,2,3-triazol-1-yl)quinoline (10a). 1-Ethynyl-1-cyclohexene (9a) was used as the starting material. $^1$H NMR (500 MHz, CD$_3$OD) δ ppm: 1.71-1.79 (m, 2H), 1.82-1.86 (m, 2H), 2.26-2.28 (m, 2H), 2.48-2.49 (m, 2H), 6.62 (m, 1H), 7.36 (d, J=8.5 Hz, 1H), 7.79 (d, J=8.5 Hz, 1H), 7.83 (dd, J=4 and 8.5 Hz, 1H), 8.22 (s, 1H), 8.39 (d, J=8.5 Hz, 1H), 9.02 (d, J=4 Hz, 1H). $^{13}$C NMR (125 MHz, CD$_3$OD) δ ppm: 23.4, 23.7, 26.4, 27.5, 113.1, 123.7, 124.7, 126.0, 126.6, 127.0, 127.7, 128.3, 136.0, 137.4, 148.6, 150.9, 154.4. HRMS (ESI): calc'd for C$_{17}$H$_{16}$N$_4$O [M+H]+: 293.1397, found: 293.1394.

8-Hydroxy-5-(4-phenyl-1H-1,2,3-triazol-1-yl)quinoline (10b). Ethynylbenzene (9b) was used as the starting material. $^1$H NMR (500 MHz, CD$_3$OD) δ ppm: 7.30 (d, J=8.5 Hz, 1H), 7.41 (dd, J=1.5 and 7.5 Hz, 1H), 7.49 (t, J=7.5 Hz, 2H), 7.70 (dd, J=4.5 and 9.5 Hz, 1H), 7.77 (d, J=8.5 Hz, 1H), 7.96 (dd, J=1.5 and 8.5 Hz, 2H), 8.21 (d, J=8.5 Hz, 1H), 8.74 (s, 1H), 8.97 (dd, J=1.5 and 4.5 Hz, 2H). $^{13}$C NMR (125 MHz, CD$_3$OD) δ ppm: 111.7, 127.0, 127.1, 129.8, 130.2, 131.5, 134.3, 138.4, 149.2, 149.9, 155.9. HRMS (ESI): calc'd for C$_{17}$H$_{12}$N$_4$O [M+H]+: 289.1084, found: 289.1076.

8-Hydroxy-5-(4-(3,5-bis(trifluoromethyl)phenyl)-1H-1,2,3-triazol-1-yl)quinoline (10c) 1-Ethynyl-3,5-bis(trifluoromethyl)benzene (9c) was used as the starting material. $^1$H NMR (500 MHz, CD$_3$OD) δ ppm: 7.38 (d, J=8.5 Hz, 1H), 7.84 (dd, J=4.5 and 8.5 Hz, 1H), 7.87 (d, J=8.5 Hz, 1H), 7.99 (s, 1H), 8.52 (dd, J=1.5 and 8.5 Hz, 1H), 8.57 (s, 1H), 9.03 (dd, J=1.5 and 4.5 Hz, 1H), 9.07 (s, 1H). $^{13}$C NMR (125 MHz, CD$_3$OD) δ ppm: 113.2, 122.8, 123.8, 124.6, 124.8, 125.7, 125.9 126.6, 127.0, 127.9, 133.6, 134.4, 146.4, 148.6, 154.5. HRMS (ESI): calc'd for C$_{19}$H$_{10}$F$_6$N$_4$O [M+H]+: 425.0832, found: 425.0836.

8-Hydroxy-5-(4-(3-chlorophenyl)-1H-1,2,3-triazol-1-yl)quinoline (10d). 1-Chloro-3-ethynylbenzene (9d) was used as the starting material. $^1$H NMR (500 MHz, CD$_3$OD) δ ppm: 7.34 (d, J=8.5 Hz, 1H), 7.41 (d, J=8 Hz, 1H), 7.48 (t, J=8 Hz, 1H), 7.77 (dd, J=4.5 and 8.5 Hz, 1H), 7.81 (dd, J=8 Hz, 1H), 7.90 (d, J=8 Hz, 1H), 8.01 (s, 1H), 8.32 (dd, J=1.5 and 8.5 Hz, 1H), 8.82 (s, 1H), 9.01 (dd, J=1.5 and 4.5 Hz, 1H). $^{13}$C NMR (125 MHz, CD$_3$OD) δ ppm: 112.3, 124.7, 125.2, 125.6, 125.7, 126.4, 126.8, 127.4, 129.6, 131.8, 133.6, 135.6, 136.2, 137.4, 147.9, 149.4, 155.4. HRMS (ESI): calc'd for C$_{17}$H$_{11}$ClN$_4$O [M+H]+: 323.0621, found: 323.0625.

8-Hydroxy-5-(4-p-tolyl-1H-1,2,3-triazol-1-yl)quinoline (10i) 1-Ethynyl-4-methylbenzene (9i) was used as the starting material. $^1$H NMR (500 MHz, CD$_3$OD) δ ppm: 2.40 (s, 3H), 7.31 (d, J=8.5 Hz, 1H), 7.41 (d, J=8.5 Hz, 1H), 7.83-7.88 (m, 2H), 7.84 (d, J=8 Hz, 1H), 7.88 (d, J=8 Hz, 1H), 8.50 (d, J=8.5 Hz, 1H), 8.72 (s, 1H), 9.04 (dd, J=1.5 and 4.5 Hz, 1H). $^{13}$C NMR (125 MHz, CD$_3$OD) δ ppm: 21.4, 113.4, 124.6, 124.7, 126.0, 126.7, 126.9, 128.0, 128.6, 130.8, 138.0, 140.0, 148.4, 149.5, 154.2. HRMS (ESI): calc'd for C$_{17}$H$_{11}$C1N$_4$O [M+H]+: 323.0694, found: 323.0702.

8-Hydroxy-5-(4-(4-bromophenyl)-1H-1,2,3-triazol-1-yl) quinoline (10u) 1-Bromo-4-ethynylbenzene (9u) was used as the starting material. $^1$H NMR (500 MHz, CDCl$_3$) δ ppm: 7.28 (d, J=8 Hz, 1H), 7.56 (dd, J=4 and 8.5 Hz, 1H), 7.60-7.64 (m, 2H), 7.61 (d, J=8 Hz, 1H), 7.81-7.83 (m, 1H), 7.82 (d, J=8.5 Hz, 1H), 8.11 (s, 1H), 8.16 (d, J=8.5 Hz, 1H), 8.90 (d, J=3.5 Hz, 1H). $^{13}$C NMR (125 MHz, CDCl$_3$) δ ppm: 108.9, 122.2, 122.5, 123.5, 124.2, 124.3, 125.1, 127.4, 129.0, 132.1, 132.2, 137.7, 146.9, 148.9, 153.9. HRMS (ESI): calc'd for C$_{17}$H$_{11}$BrN$_4$O [M+H]+: 367.0189, found: 367.0187.

5-Azido-8-hydroxy-2-methylquinoline (13). 5-Amino-8-hydroxy-2-methylquinoline (12; 723 mg, 4.2 mmol) was dissolved in a solution of concentrated hydrochloric acid (0.4 mL) and water (5 mL), cooled to −3° C. in a salt-ice bath, stirred for 10 min, then treated dropwise with a cold solution of sodium nitrite (0.50 g, 7.2 mmol) in water (5 mL). The mixture was stirred for 20 min, then treated dropwise with sodium azide (0.60 g, 9.2 mmol) in water (40 mL), stirred at 0° C. for a further 1.5 h, then allowed to warm to room temperature over 24 h in the dark. Isolation by extraction with diethyl ether gave a dark brown solid, which was recrystallized from light petroleum to yield 13 as light brown crystals (554 mg, 66%). $^1$H NMR (500 MHz, CD$_3$OD) δ ppm: 3.31 (s, 3H), 7.06 (d, J=8.5 Hz, 1H), 7.15 (d, J=8.5 Hz, 1H), 7.36 (d, J=8.5 Hz, 1H), 8.21 (d, J=8.5 Hz, 1H). $^{13}$C NMR (125 MHz, CD$_3$OD) δ ppm: 24.9, 111.8, 115.6, 121.6, 123.7, 127.9, 132.6, 139.6, 151.1, 159.7. HRMS (ESI): calcd for C$_{10}$H$_8$N$_4$O [M+H]+: 201.0771, found: 201.0773.

5-Azido-8-tert-butyldiphenylsilyloxy-2-methylquinoline (14). A 100-mL flask was successively loaded with dry DMF (10 mL), 13 (200 mg, 1 mmol), imidazole (68.08 mg, 1 mmol), and tert-butyldiphenylsilyl chloride (302 mg, 1.1 mmol). The solution was stirred at room temperature for 10 h, diluted with ethyl acetate (500 mL), washed with aqueous HCl (0.1 M, 50 mL), brine (100 mL), water (100 mL), dried over Na$_2$SO$_4$ and evaporated under reduced pressure to afford 8.41 g (96%) of protected product as a colorless oil (428 mg, 98%). $^1$H NMR (500 MHz, CDCl$_3$) δ ppm: 1.19 (s, 9H), 2.33 (s, 3H), 6.98 (d, J=8.5 Hz, 1H), 7.06 (d, J=8.5 Hz, 1H), 7.10 (d, J=8.5 Hz, 1H), 7.38-7.26 (m, 6H), 7.81-7.79 (m, 4H), 8.11 (d, J=8.5 Hz, 1H). $^{13}$C NMR (125 MHz, CDCl$_3$) δ ppm: 20.1, 24.3, 26.8, 113.5, 116.7, 120.6, 121.8, 127.3, 128.4, 129.2, 130.6, 134.3, 135.1, 140.9, 148.9, 157.9. HRMS (ESI): calc'd for C$_{26}$H$_{26}$N$_4$OSi [M+H]+: 438.1876, found: 438.1879.

5-Azido-2-bromomethyl-8-tert-butyldiphenylsilyloxyquinoline (15). NBS (165.5 mg, 0.93 mmol) and AIBN (152.7 mg, 0.93 mmol) were added to a solution of 14 (371 mg, 0.85 mmol) in CCl$_4$ (4.5 mL), and the mixture was refluxed 20 min and evaporated to dryness. The residue was dissolved in CH$_2$Cl$_2$ (20 mL), the solution was washed with H$_2$O (5 mL) and brine (5 mL), dried over Na$_2$SO$_4$, and evaporated. The residue was purified by flash chromatography, using 20-50% gradient of EtOAc in hexane as eluent, to yield the unresolved (3:1) mixture of 14 and 15 (131.6 mg, 30%). $^1$H NMR (500 MHz, CDCl$_3$) δ ppm: 1.16 (s, 9H), 4.24 (s, 2H), 6.97 (d, J=8.5 Hz, 1H), 7.03 (d, J=8.5 Hz, 1H), 7.09 (d, J=8.5 Hz, 1H), 7.26-7.43 (m, 6H), 7.76-7.78 (m, 4H), 8.24 (d, J=8.5 Hz, 1H). HRMS (ESI): calc'd for C$_{26}$H$_{25}$BrN$_4$OSi [M+H]+: 517.1054, found: 517.1050.

Stock solutions. Due to the affinity of the phosphorylated peptides for selected transition metal ions, by analogy with previously reported peptides, only reagents of the highest purity and lowest metal content were used to avoid the need to remove metal ion impurities after preparation.

1. Stock solutions of the peptides were prepared in doubly deionized water and concentrations were determined by UV-Vis (based on the determined extinction coefficient of the fluorophore moiety, either 1 (Sox), $\epsilon_{355}$=8247 M$^{-1}$ cm$^{-1}$ or 10u (Clk), $\epsilon_{360}$=7905 M$^{-1}$ cm$^{-1}$ in 0.1 M NaOH with 1 mM Na$_2$EDTA). An average of the values from three separate solutions, each prepared using a different volume of the stock solution, was read on UV-Vis spectrophotometer. Purified peptide stock solutions could be stored at 4° C. for at least 6 months or −20° C. for longer periods.

2. 500 mM HEPES (SigmaUltra) was prepared and adjusted to pH 7.4 with NaOH (99.998+%, Aldrich) solution.

3. 10 mM DTT (Biotechnology grade, Mallinckrodt) was prepared in degassed ultrapure water and stored in aliquots at −80° C.

4. 500 mM EGTA (SigmaUltra) was prepared in 2 M NaOH and stored at 4° C.

5. A magnesium chloride stock solution of 2.66 M was prepared using Alfa Aesar Puratronic grade salts. Most commercially available salts contain Zn$^{2+}$ as significant impurities and should not be used due to the high affinity of the phosphorylated peptides for Zn$^{2+}$. The Mg$^{2+}$ concentration was determined by titration with a standardized solution of EDTA (Aldrich) in the presence of an Eriochrome Black T (Aldrich) as described previously.

6. 500 mM HEPES (SigmaUltra) was prepared and adjusted to pH 7.4 with NaOH (99.998+%, Aldrich) solution.

7. 20 mg/mL BSA (Heat Shock Fraction V, Roche) was prepared in ultrapure water, filtered through a 0.45 micron syringe filter to remove particulates and stored at 4° C.

8. 100 mM ATP (Disodium salt, Low Metals Grade, Calbiochem) was prepared in ultrapure water. The solution was stored in aliquots at −80° C.

Figure 9:
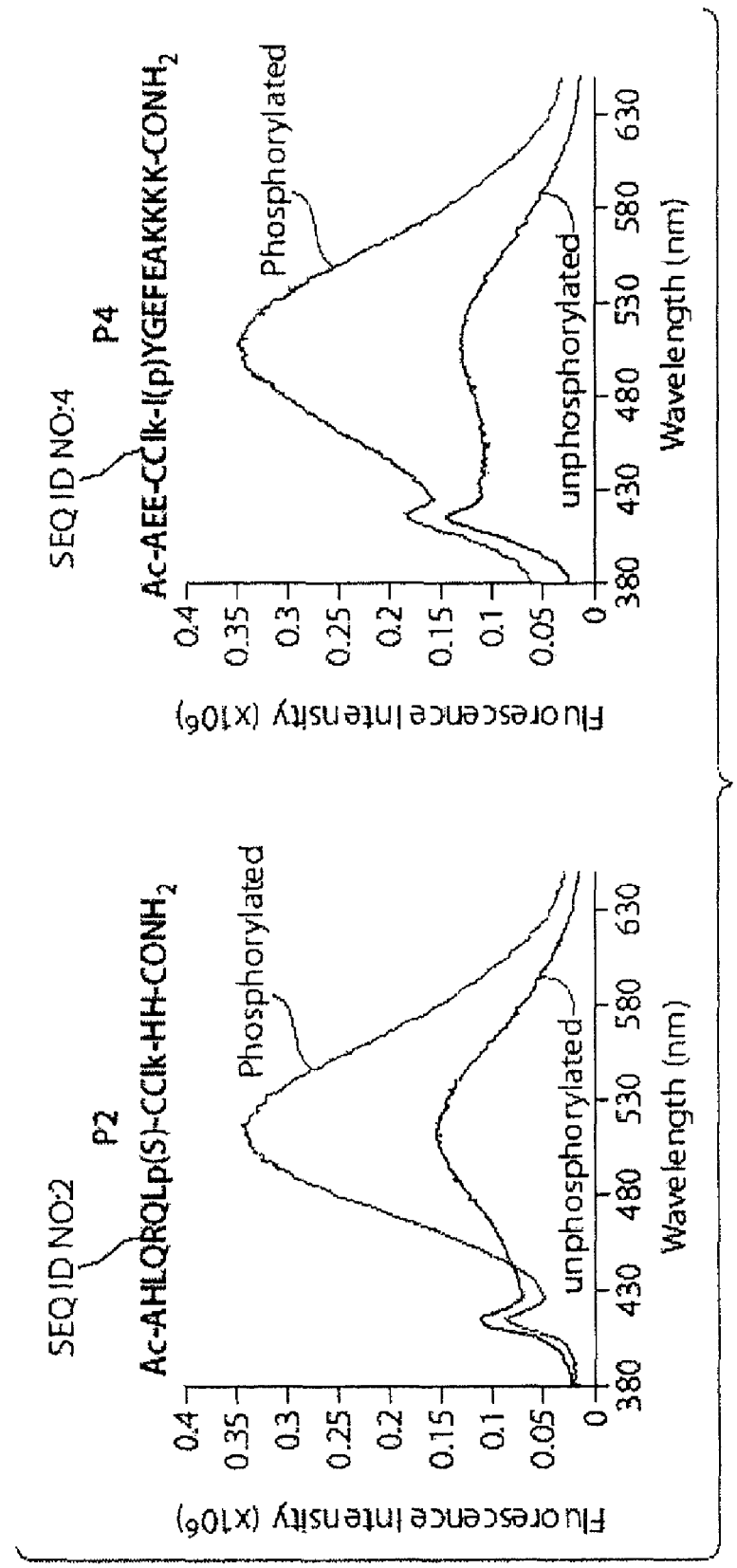
FIG. 9 shows a spectral comparison of phosphorylated and unphosphorylated peptides.
Figure 10:
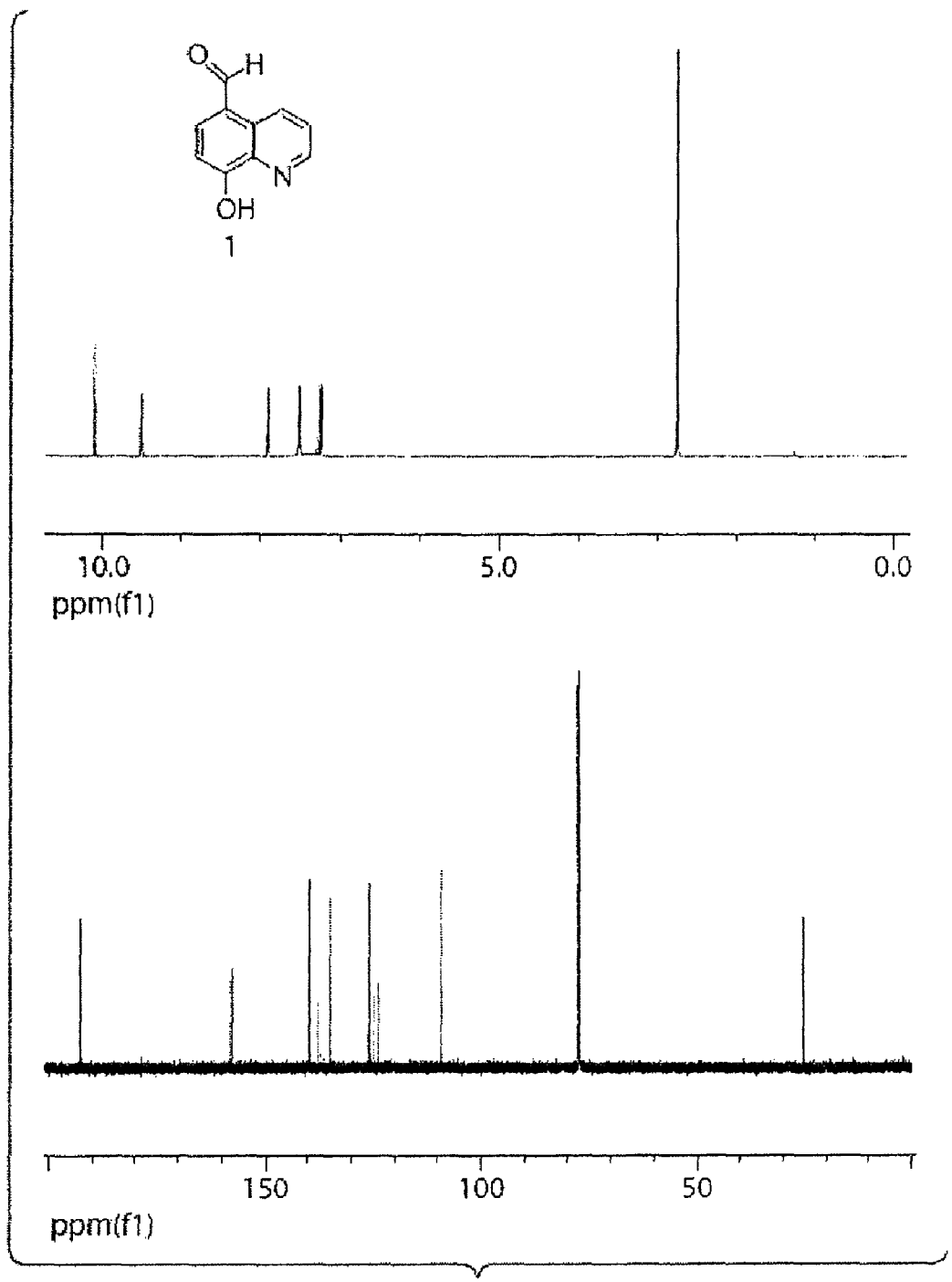
FIG. 10 shows NMR spectra for 5-carbaldehyde-8-hydroxy-2-methylquinoline (2), according to an embodiment.
Figure 11:
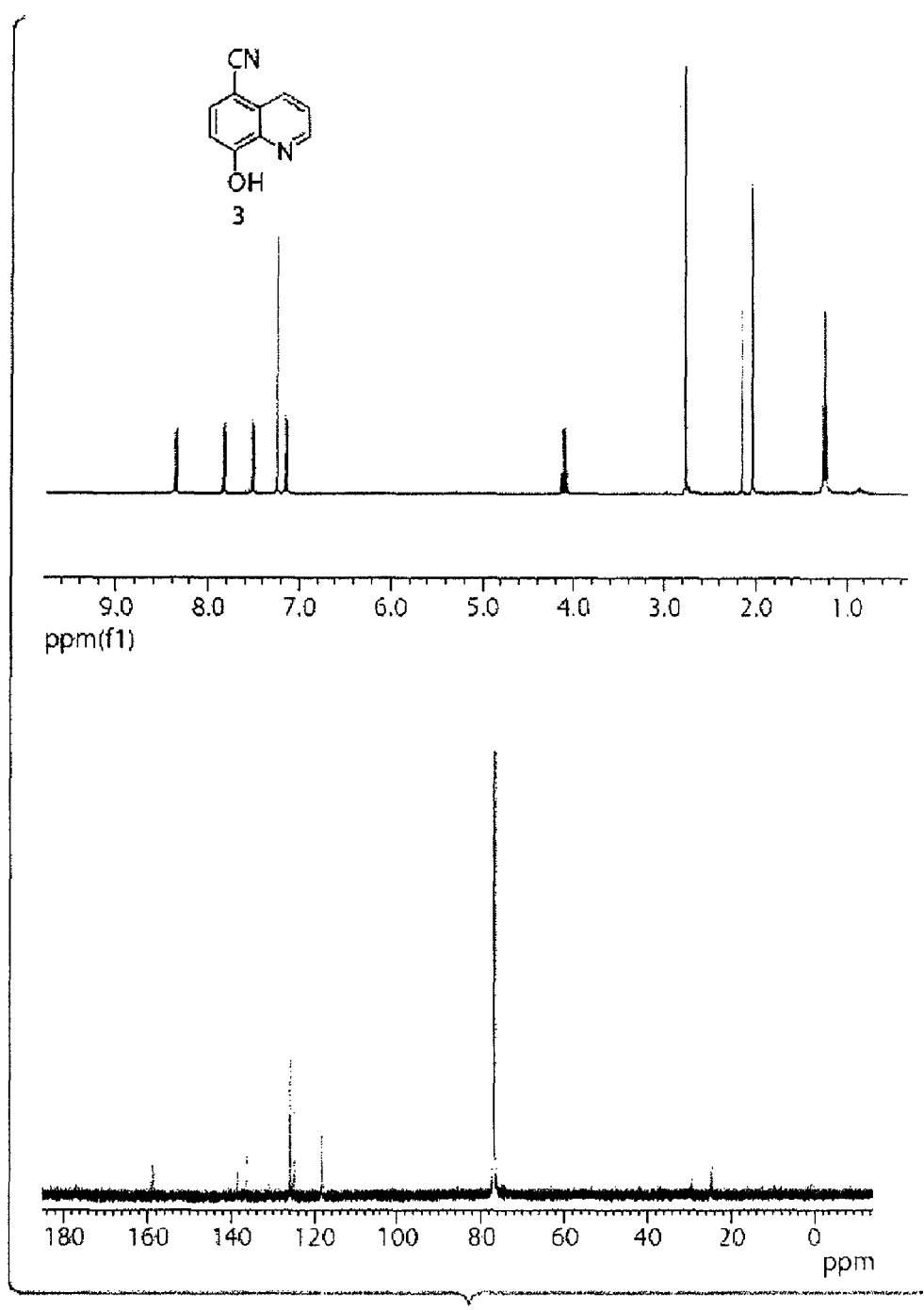
FIG. 11 shows NMR spectra for 5-carbonitrile-8-hydroxy-2-methylquinoline (3), according to an embodiment.
Figure 12:
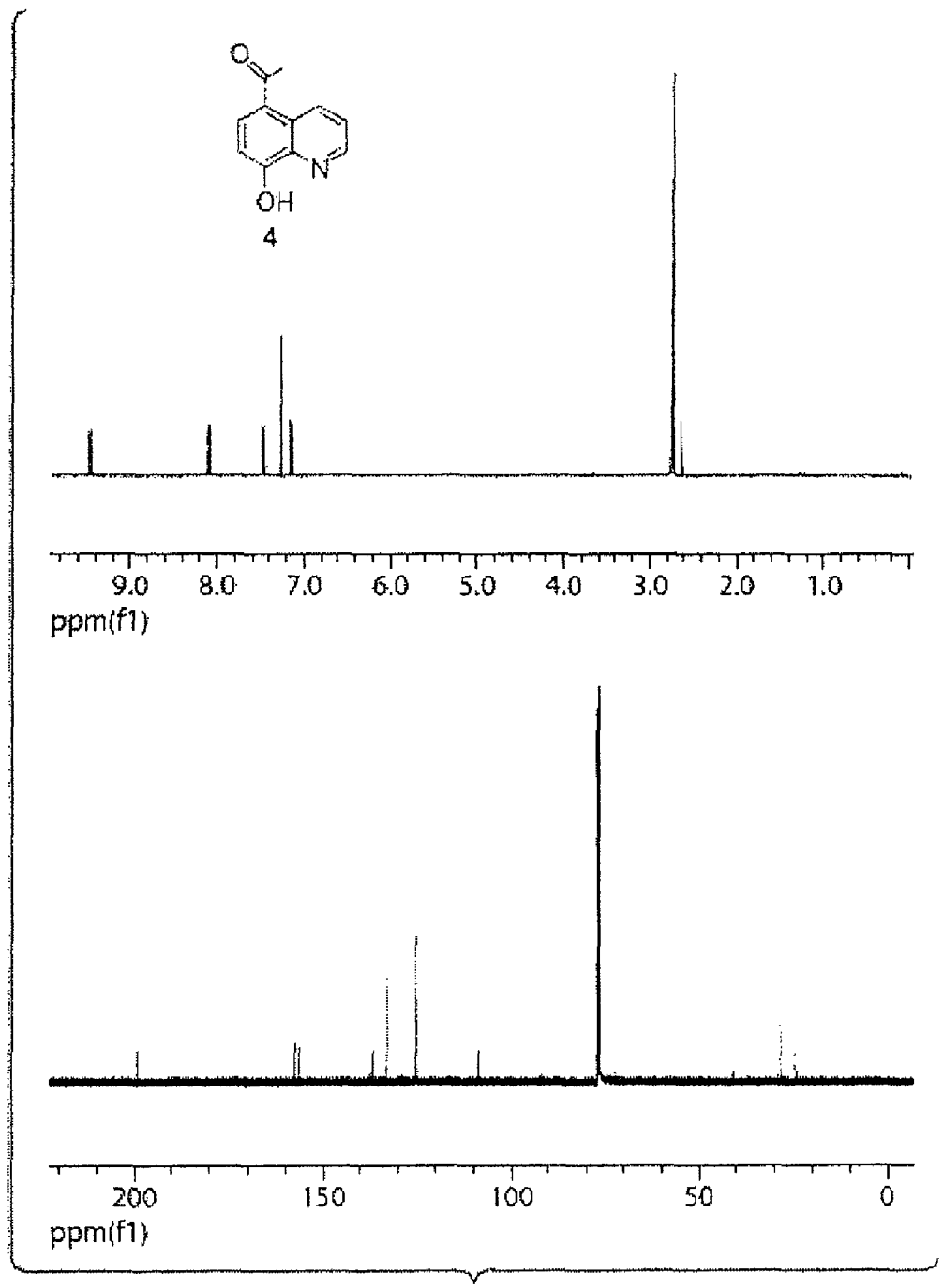
FIG. 12 shows proton (top) and carbon (bottom) NMR spectra for 1-(8-Hydroxy-2-methylquinolin-5-yl)ethanone (4).
Figure 13:
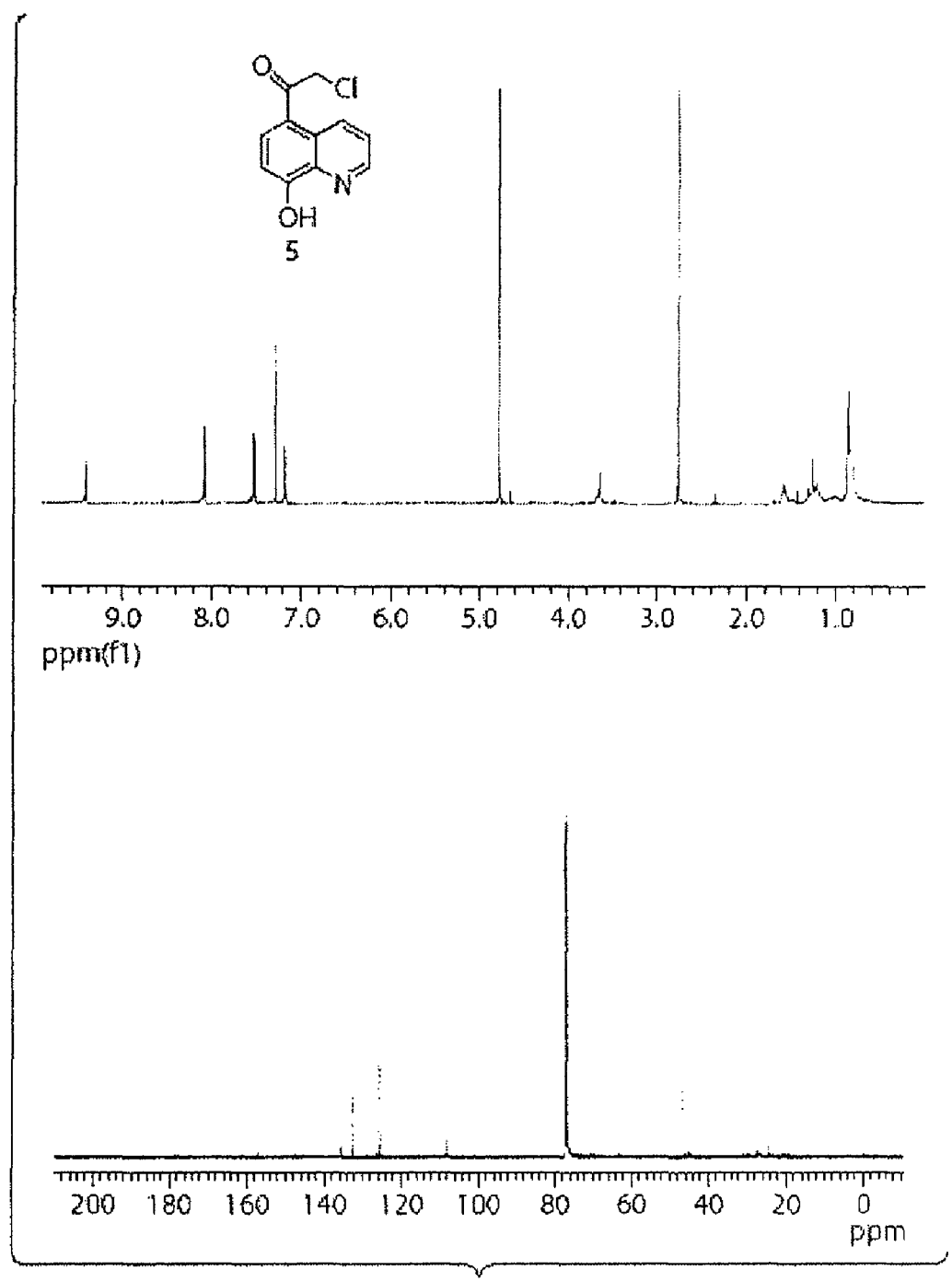
FIG. 13 shows proton (top) and carbon (bottom) NMR spectra for 8-Hydroxy-2-methylquinoline-5-Carbonyl chloride (5).
Figure 14:
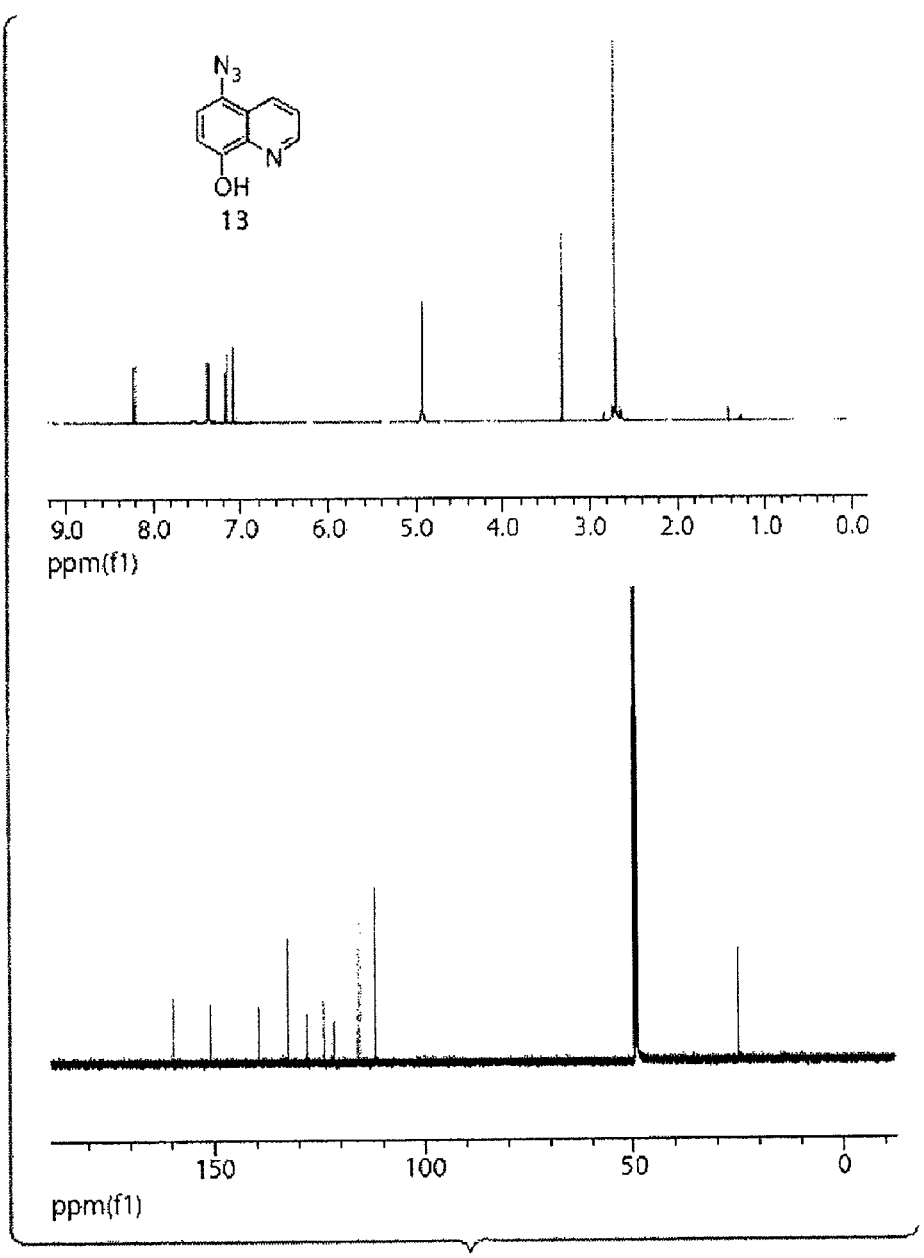
FIG. 14 shows NMR spectra for 5-Azido-8-hydroxy-2-methylquinoline (13), according to an embodiment.
Figure 15:
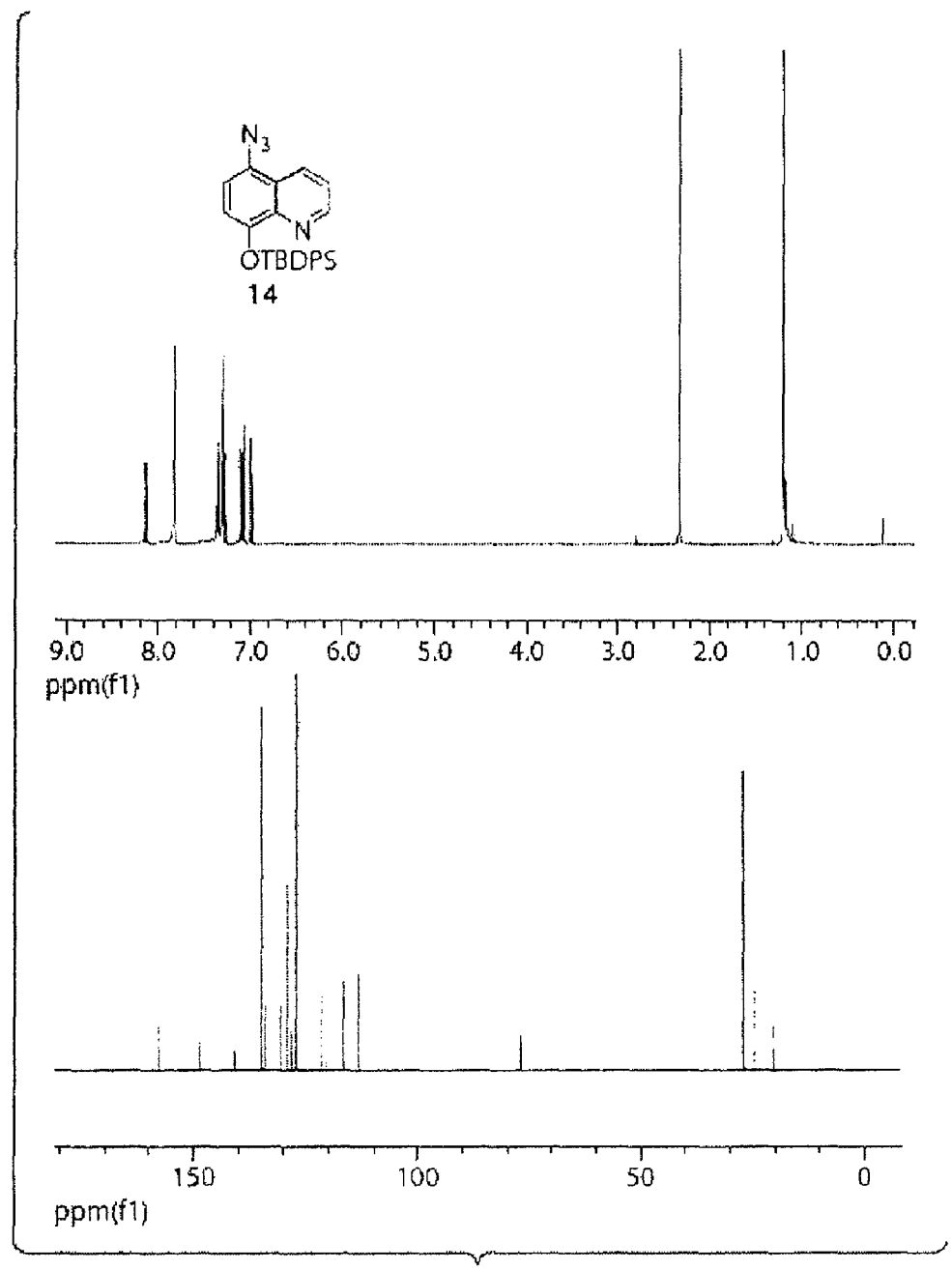
FIG. 15 shows proton (top) and carbon (bottom) NMR spectra for 5-Azido-8-tert-butyldiphenylsilyloxy-2-methylquinoline (14).
Figure 16:
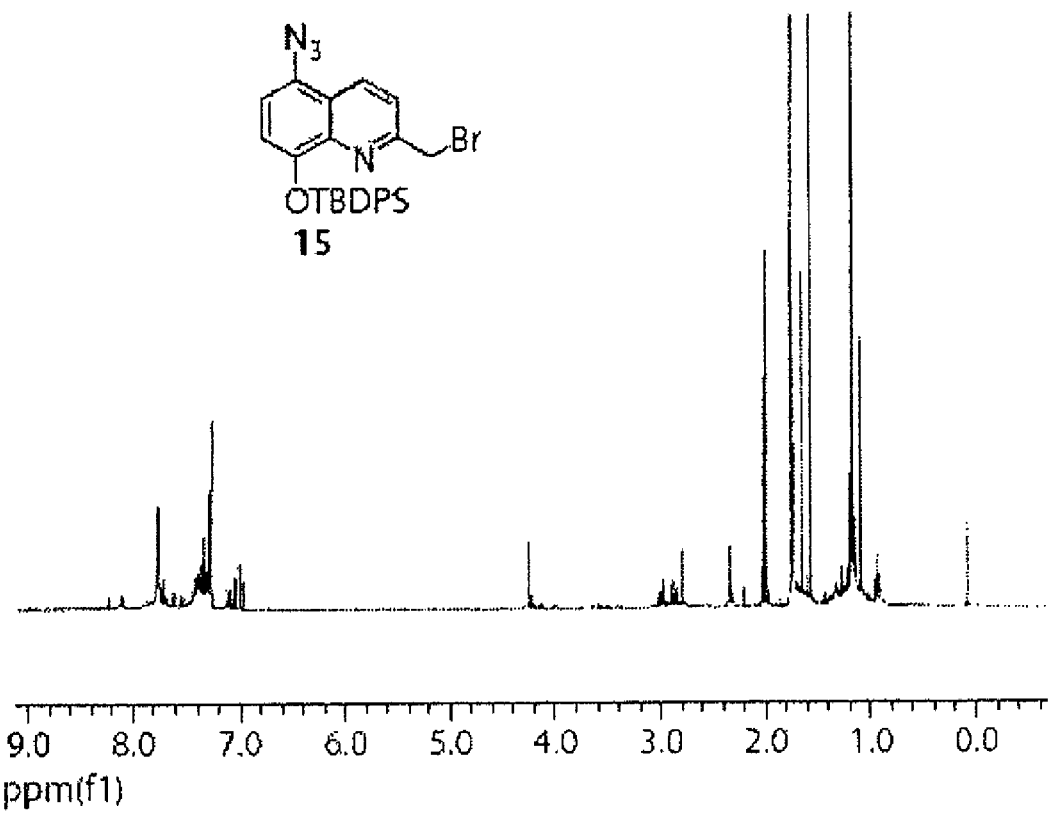
FIG. 16 shows the proton NMR spectrum for 5-Azido-2-bromomethyl-8-tert-butyldiphenylsilyloxyquinoline (15).
Figure 17:
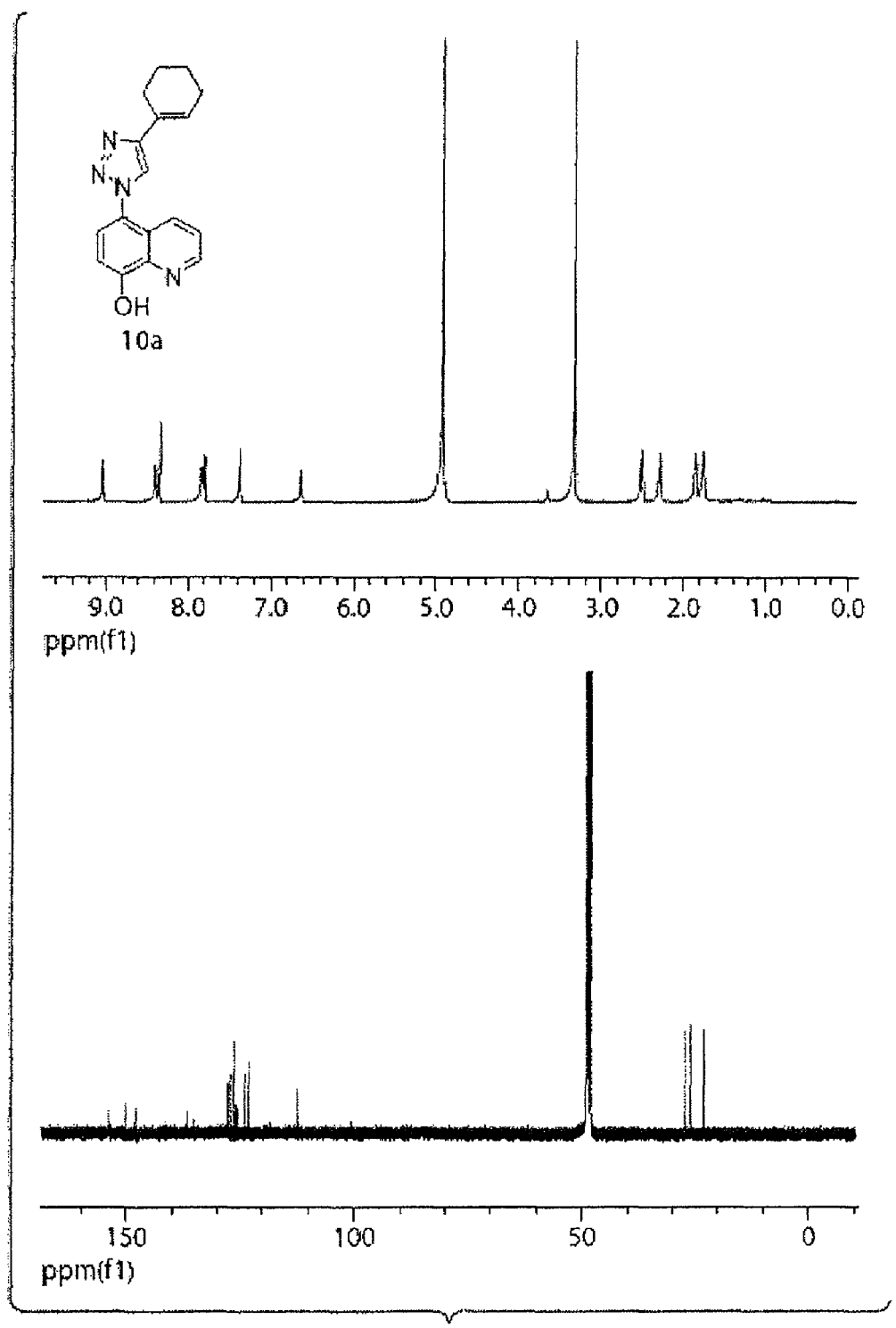
FIG. 17 shows proton (top) and carbon (bottom) NMR spectra for 8-Hydroxy-5-(4-cyclohexenyl-1H-1,2,3-triazol-1-yl)quinoline (10a).
Figure 18:
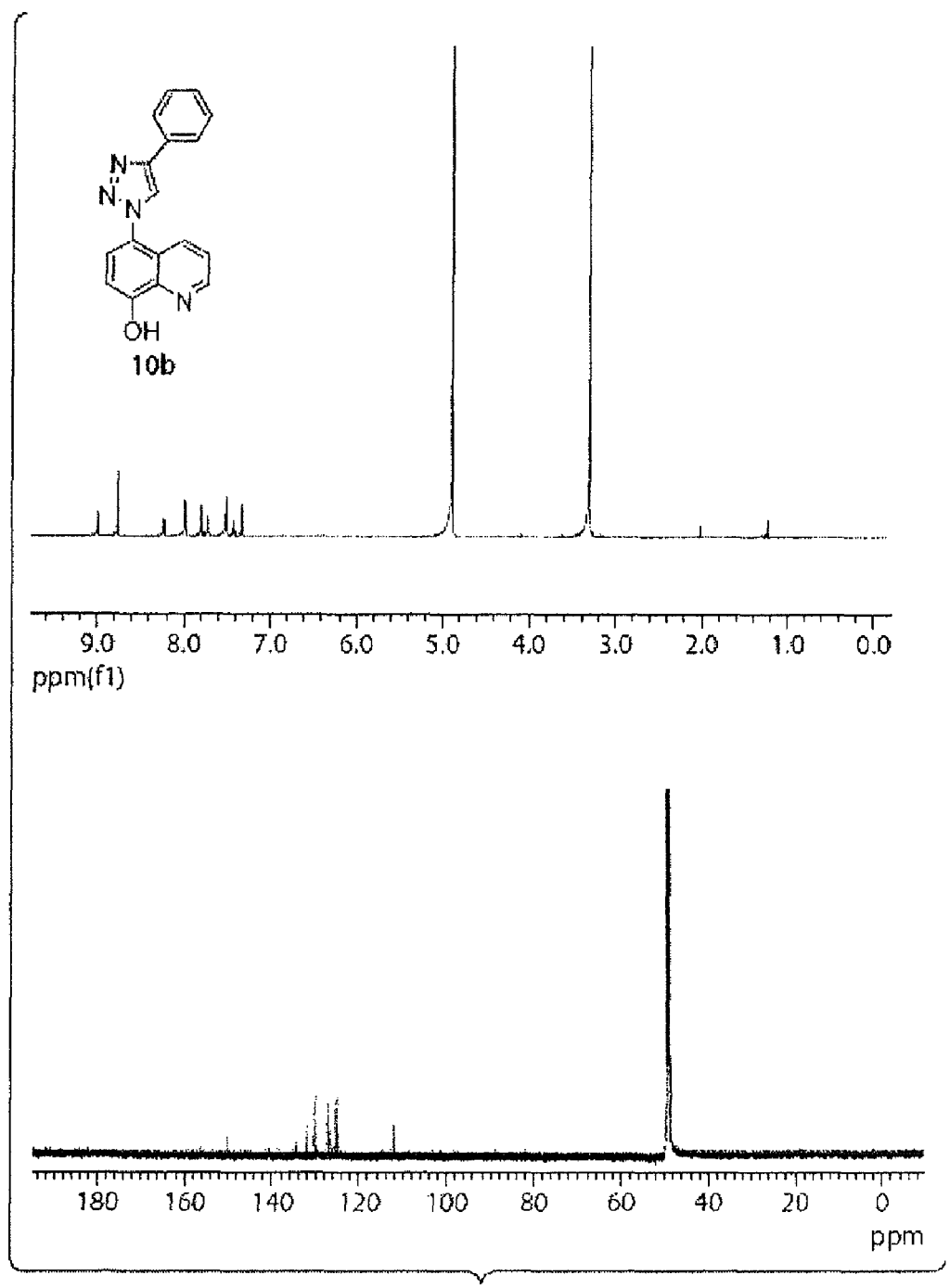
FIG. 18 shows proton (top) and carbon (bottom) NMR spectra for 8-Hydroxy-5-(4-phenyl-1H-1,2,3-triazol-1-yl)quinoline (10b).
Figure 19:
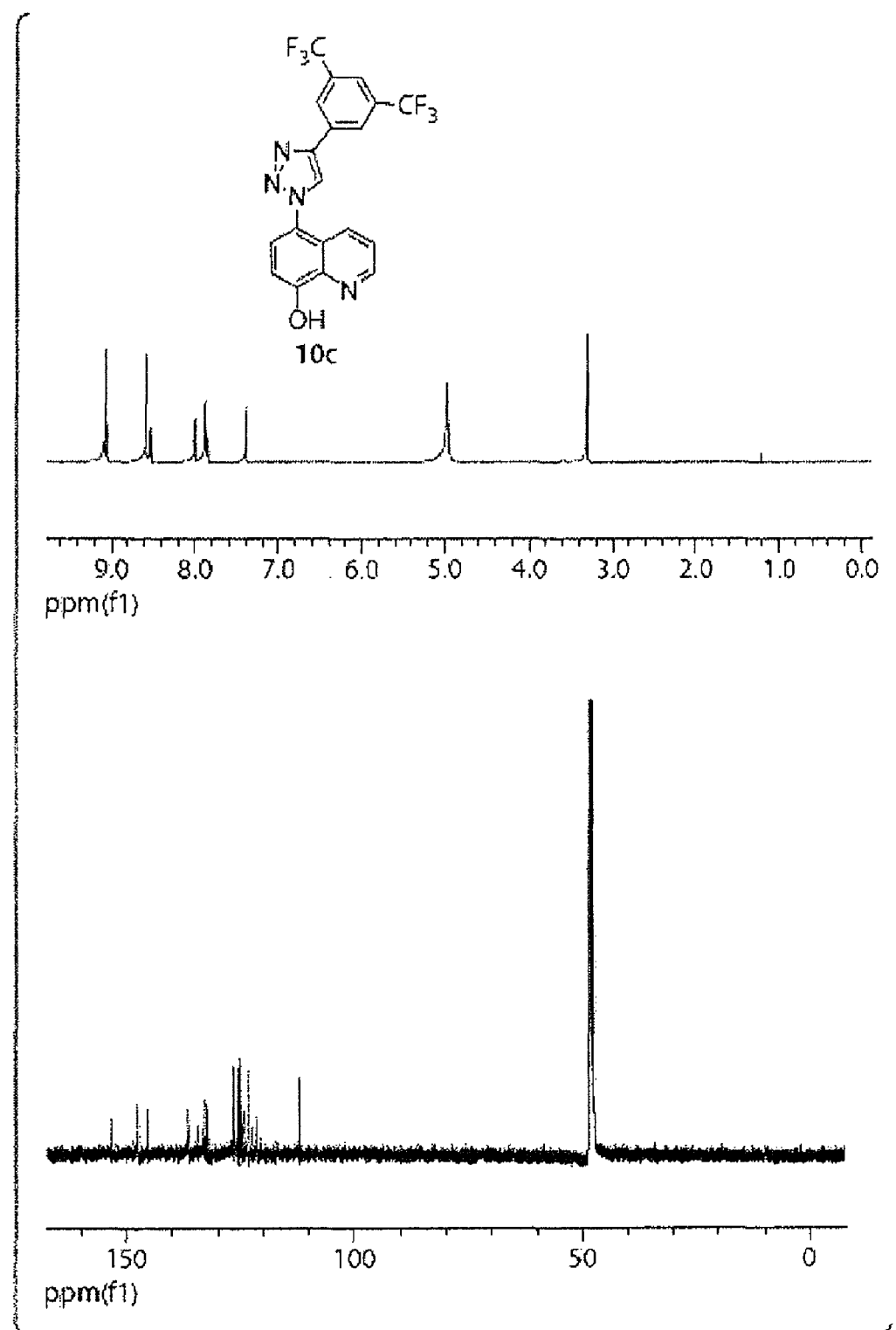
FIG. 19 shows proton (top) and carbon (bottom) NMR spectra for 8-Hydroxy-5-(4-(3,5-bis(trifluoromethyl)phenyl)-1H-1,2,3-triazol-1-yl)quinoline (10c).
Figure 20:
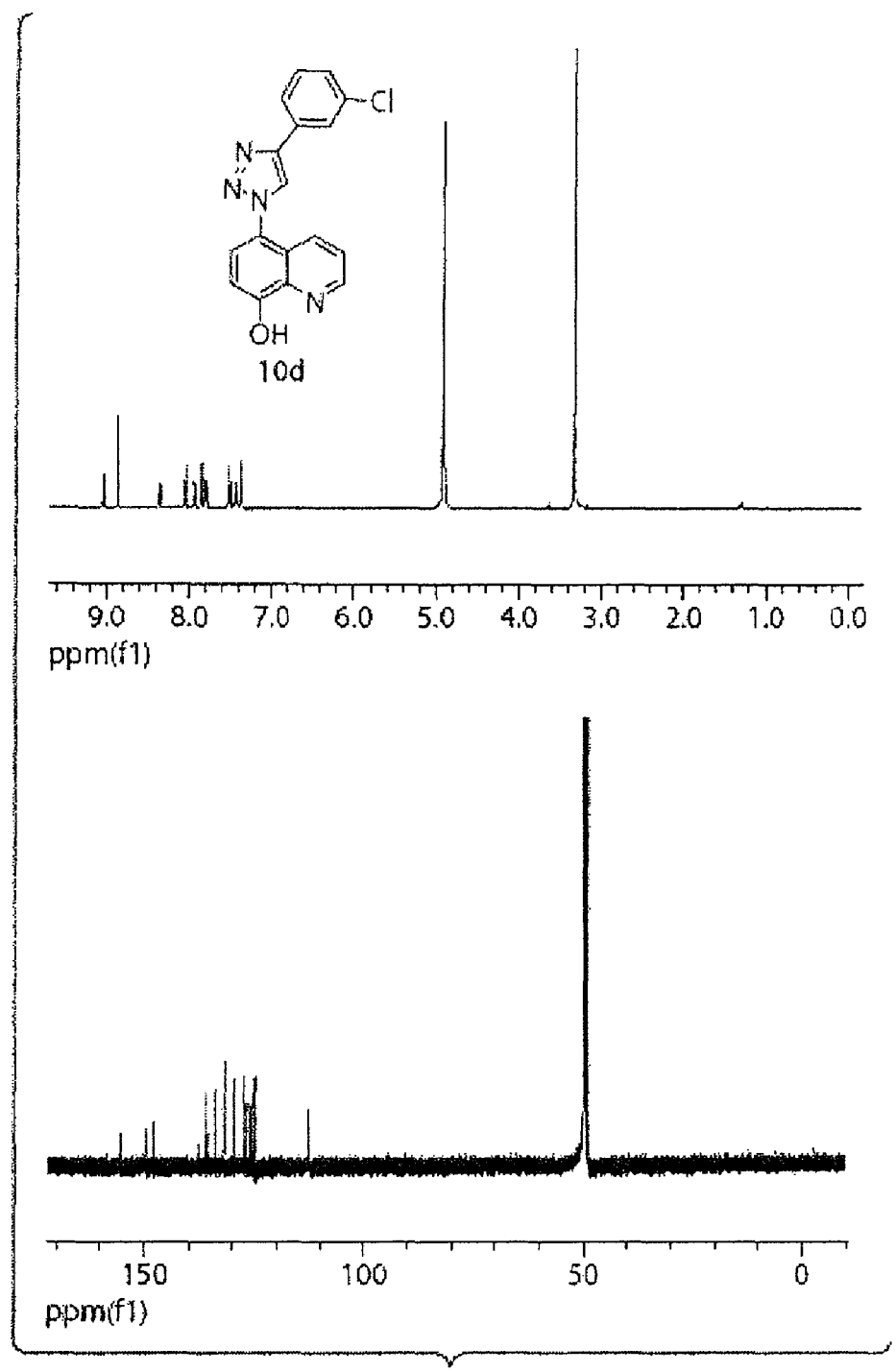
FIG. 20 shows proton (top) and carbon (bottom) NMR spectra for 8-Hydroxy-5-(4-(3-chlorophenyl)-1H-1,2,3-triazol-1-yl)quinoline (10d).
Figure 21:
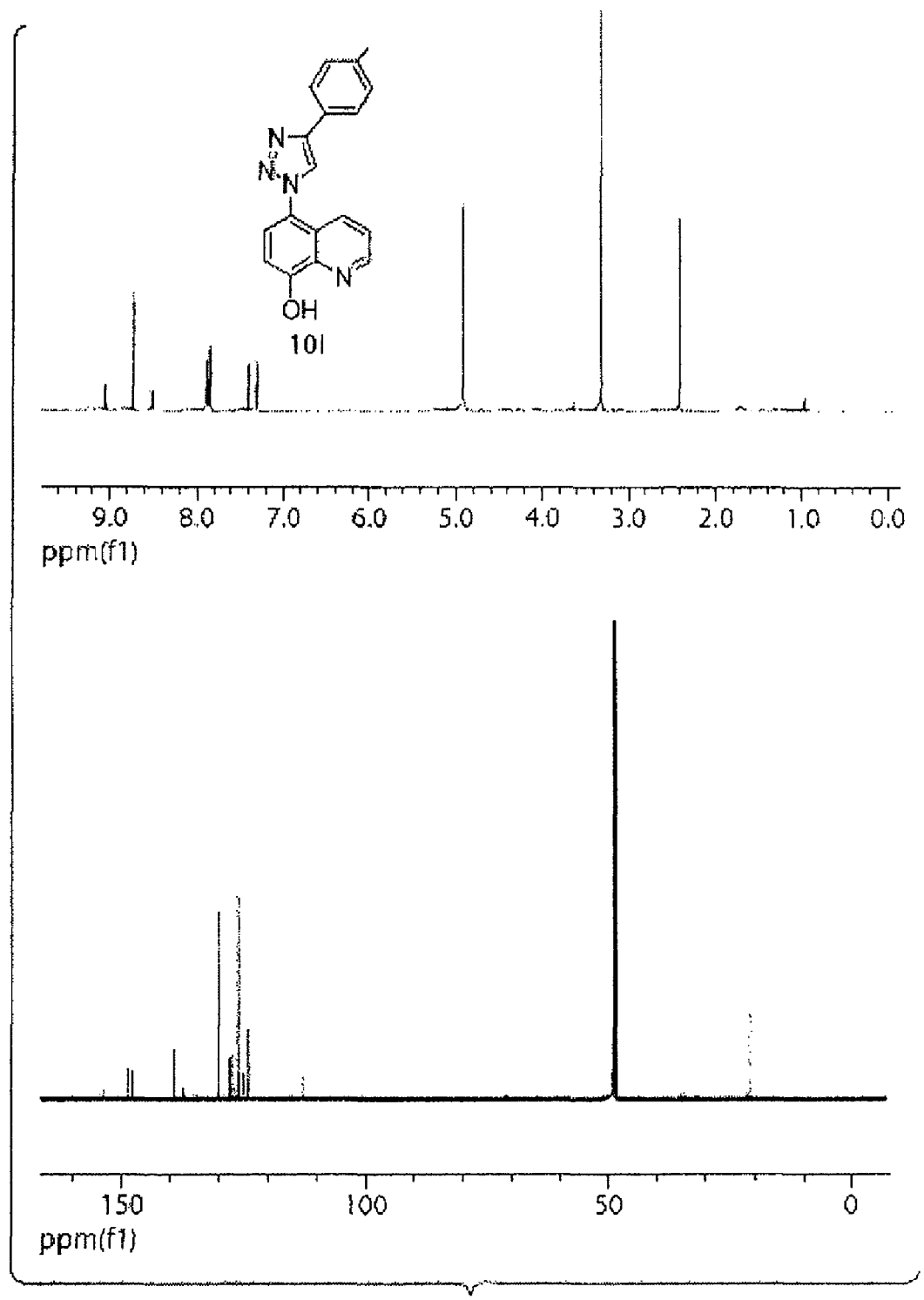
FIG. 21 shows proton (top) and carbon (bottom) NMR spectra for 8-Hydroxy-5-(4-p-tolyl-1H-1,2,3-triazol-1-yl)quinoline (10i).
Figure 22:
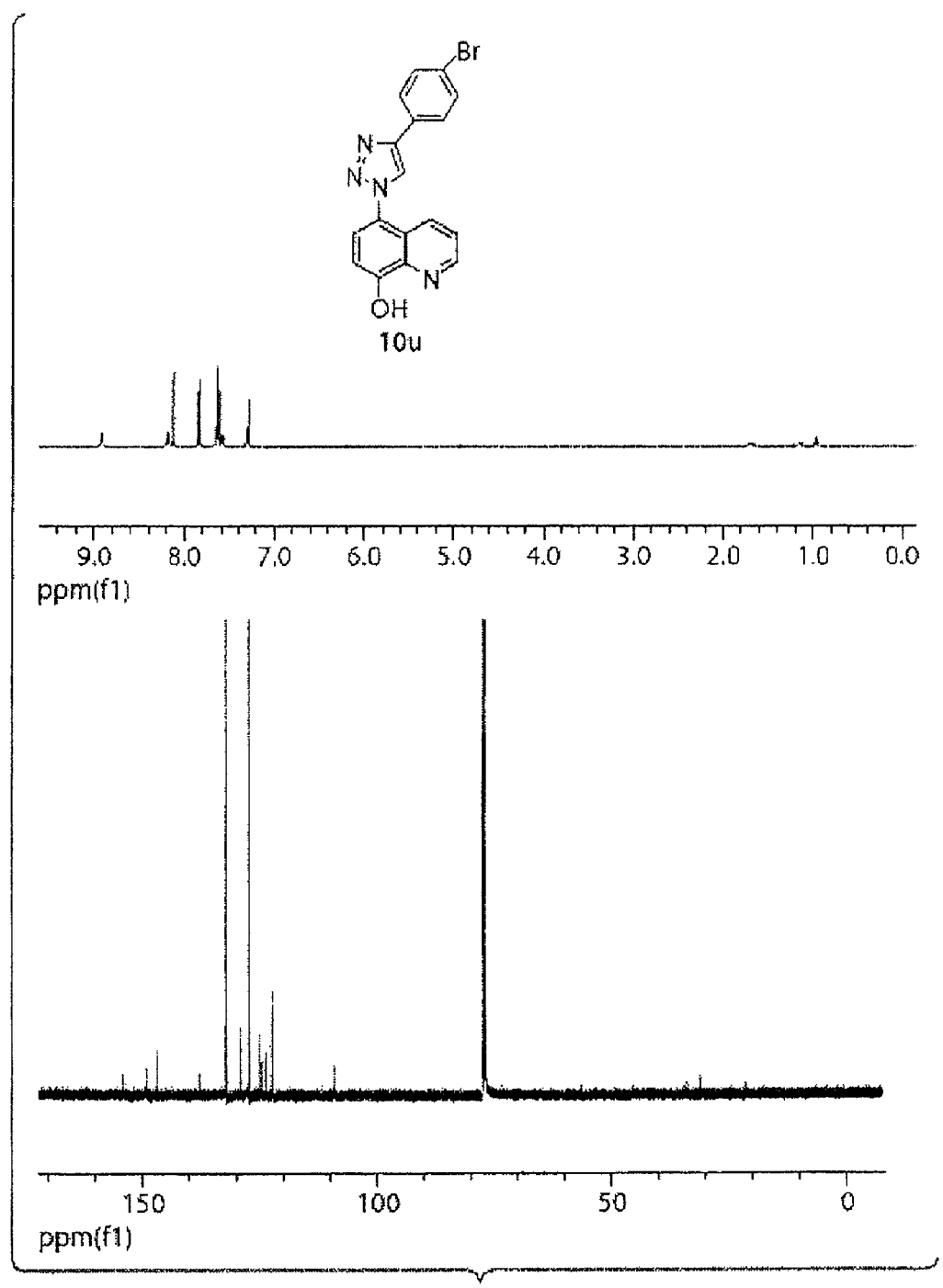
FIG. 22 shows proton (top) and carbon (bottom) NMR spectra for 8-Hydroxy-5-(4-(4-bromophenyl)-1H-1,2,3-triazol-1-yl)quinoline (10u).

Fluorescence Experiments.

a. Fluorescence analysis of 8-hydroxyquinoline click products. A 96-well microtier plate was used in the experiments for preliminary examination of fluorescence properties. The overall volume in each well was 200 microliters. Individual reactions contained the crude product from the click chemistry reaction (10 micromolar dissolved in DMSO), MgCl$_2$ (10 mM), NaCl (150 mM) and HEPES (50 mM) at 25° C. (pH 7.4). The fluorescence spectra were recorded with fixed excitation at 370 nm and emission at 525 nm. The excitation and emission wavelengths for each fluorophore are summarized in FIG. 8. Based on the preliminary screening, selected products were then synthesized in larger quantities and the quantum yields of the corresponding hydroxyquinoline derivatives were determined.

b. Extinction coefficient determination. Extinction coefficients of 1 and 10u were measured in 50 mM HEPES (pH 7.0), 150 mM NaCl. The $\epsilon_{max}$ values were determined by plotting absorbance at 360 nm versus concentration for four chromophore solutions with concentrations between 20 and 60 micromolar and including 1 mM MgCl$_2$.

c. Quantum yield determination. The quantum yield (Φ) was determined in 20 mM HEPES (pH 7.4). Quinine sulphate dihydrate (QS, Fluka, puriss. for fluorescence) in 0.1 M H2SO4 was used as a standard (Φ=0.55). A 4 micromolar solution of the corresponding oxine derivative with 50 mM MgCl$_2$ was compared to a 4 micromolar solution of quinine sulfate to assure that the absorbance (A$_{360}$) is less than 0.05 at identical excitation wavelengths. The following equation was used to calculate the quantum yield:

$$\Phi = IA_{QS}\Phi_{QS}/AI_{QS}$$

where $A=A_{360}$ and I=integrated fluorescence intensity ($\lambda_{ex}$=360 nm). The calculated $\Phi$ assumes that the refractive index of 0.1 M $H_2SO_4$ is identical to that of 20 mM HEPES (pH 7.4). The error associated with the $\Phi$ of quinine sulfate is at least 10%, the error in $\Phi$ is no less than 10%.

d. Spectral comparison of phosphorylated and unphosphorylated peptides. The fluorescence spectra of 10 micromolar phosphorylated (black line) and unphosphorylated (red line) peptides in 20 mM HEPES (pH 7.4) and 10 mM $MgCl_2$ were recorded in the fluorometer (slit widths: Em=5 nm, Ex=5 nm; $\lambda_{ex}$=360 nm, $\lambda_{em}$=380-650 nm) in a quartz microcuvette (120 microliters) (FIG. 9).

e. Enzyme Experiments with MK2 and C-Sox- or C-Clk-based Substrates. Recombinant MK2 (Upstate, appropriately diluted with 20 mM HEPES [pH 7.4], 1 mM DTT, 0.1% Brij-35, and 1 mg/mL BSA) was added to initiate each reaction. The assays were performed in the fluorometer (slit widths: Em=5 nm, Ex=5 nm; $\lambda_{ex}$=360 nm, $\lambda_{em}$=485 nm) using a quartz microcuvette (120 µL) at 30° C. for 10 min. Standard assay conditions were as follows: 20 mM HEPES (pH 7.4), 10 mM $MgCl_2$, 1 mM ATP, 1 mM DTT, 0.1 mM EGTA, 0.01% Brij-35, 0.1 mg/mL BSA, 1 ng MK2. The percent turnover (% TO) for C-Sox- and C-Clk-based peptides was then calculated from fluorescence intensity after 10 min of reaction time and using previously described protocols.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:
a compound having a structure as in formula (I):

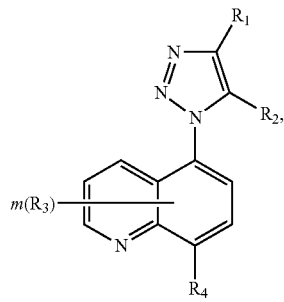

(I)

wherein $R_1$ and $R_2$ are each independently hydrogen or aryl, or wherein $R_1$ and $R_2$ together with the carbon atoms of the triazole ring to which they are connected form a ring;

$R_3$ is independently hydrogen, alkyl, aryl, halo, or hydroxyl, amino, thiol, sulfonic acid, sulfonamide, a protein kinase substrate, at least one amino acid, or a substituted derivative thereof, wherein $R_3$ can substitute any open valence of any ring within structure (I);

m is 1, 2, 3, 4, or 5; and $R_4$ is hydroxyl, amino, thiol, or a substituted derivative thereof.

2. A composition as in claim 1, wherein $R_1$ is aryl and $R_2$ is hydrogen.

3. A composition as in claim 1, wherein the compound has the following structure:

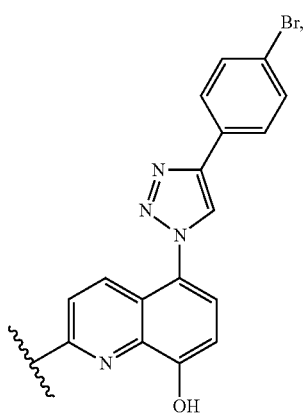 [SMILES: *c1ccc2c(-n3cc(-c4ccc(Br)cc4)nn3)ccc(O)c2n1]

wherein " ~~~ " is a protein kinase substrate or at least one amino acid.

4. A method, comprising:
determining phosphorylation of a protein kinase substrate using fluorescence of a composition of formula (I):

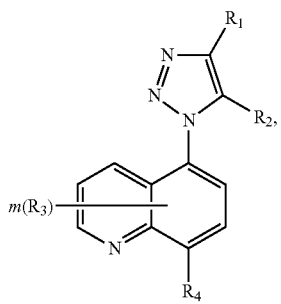

(I)

wherein $R_1$ and $R_2$ are each independently hydrogen or aryl, or where $R_1$ and $R_2$ together with the carbon atoms which they substitute form a ring;
$R_3$ is independently hydrogen, alkyl, aryl, halo, or hydroxyl, amino, thiol, sulfonic acid, sulfonamide, a protein kinase substrate, at least one amino acid, or a substituted derivative thereof, wherein $R_3$ can substitute an open valence of any ring within structure (I);
m is 1, 2, 3, 4, or 5; and
$R_4$ is hydroxyl, amino, thiol, or a substituted derivative thereof.

5. The method of claim 4, wherein $R_1$ is aryl and $R_2$ is hydrogen.

6. The method of claim 4, wherein $R_3$ is a protein kinase substrate.

7. The method of claim 4, wherein the compound has the following structure:

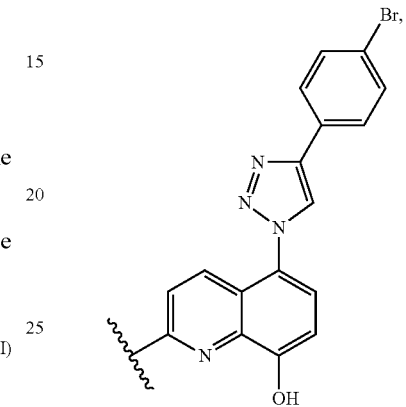

wherein " ~~~ " is a protein kinase substrate or at least one amino acid.

8. The method of claim 4,
wherein the composition has a fluorescence emission maximum greater than 490 nm.

9. The method of claim 4,
wherein the composition has a fluorescence extinction coefficient greater than 1000 $M^{-1}cm^{-1}$ at a fluorescence emission wavelength greater than 490 nm.

10. A composition as in claim 1,
wherein $R_3$ is a protein kinase substrate or at least one amino acid.

11. A composition as in claim 10, wherein $R_3$ is a protein kinase substrate.

* * * * *

SEQUENCE LISTING

<160> NUMBER OF SEQ ID NOS: 8

<210> SEQ ID NO 1
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetyl
<220> FEATURE:
<221> NAME/KEY: MISC_FEATURE
<222> LOCATION: (8)..(8)
<223> OTHER INFORMATION: O-phosphate
<220> FEATURE:
<221> NAME/KEY: MISC_FEATURE
<222> LOCATION: (10)..(10)
<223> OTHER INFORMATION: S-Sox
<220> FEATURE:
<221> NAME/KEY: MISC_FEATURE
<222> LOCATION: (12)..(12)
<223> OTHER INFORMATION: amide terminus

<400> SEQUENCE: 1

Ala His Leu Gln Arg Gln Leu Ser Ile Cys His His
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetyl
<220> FEATURE:
<221> NAME/KEY: MISC_FEATURE
<222> LOCATION: (8)..(8)
<223> OTHER INFORMATION: O-phosphate
<220> FEATURE:
<221> NAME/KEY: MISC_FEATURE
<222> LOCATION: (10)..(10)
<223> OTHER INFORMATION: S-Clk
<220> FEATURE:
<221> NAME/KEY: MISC_FEATURE
<222> LOCATION: (12)..(12)
<223> OTHER INFORMATION: amide terminus

<400> SEQUENCE: 2

Ala His Leu Gln Arg Gln Leu Ser Ile Cys His His
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetyl
<220> FEATURE:
<221> NAME/KEY: MISC_FEATURE
<222> LOCATION: (4)..(4)
<223> OTHER INFORMATION: C-Sox
<220> FEATURE:
<221> NAME/KEY: MISC_FEATURE
<222> LOCATION: (6)..(6)

```
<223> OTHER INFORMATION: O-phosphate
<220> FEATURE:
<221> NAME/KEY: MISC_FEATURE
<222> LOCATION: (15)..(15)
<223> OTHER INFORMATION: amide terminus

<400> SEQUENCE: 3

Ala Glu Glu Cys Ile Tyr Gly Glu Phe Glu Ala Lys Lys Lys Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetyl
<220> FEATURE:
<221> NAME/KEY: MISC_FEATURE
<222> LOCATION: (4)..(4)
<223> OTHER INFORMATION: C-Clk
<220> FEATURE:
<221> NAME/KEY: MISC_FEATURE
<222> LOCATION: (6)..(6)
<223> OTHER INFORMATION: O-phosphate
<220> FEATURE:
<221> NAME/KEY: MISC_FEATURE
<222> LOCATION: (15)..(15)
<223> OTHER INFORMATION: amide terminus

<400> SEQUENCE: 4

Ala Glu Glu Cys Ile Tyr Gly Glu Phe Glu Ala Lys Lys Lys Lys
1               5                   10                  15

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetyl
<220> FEATURE:
<221> NAME/KEY: MISC_FEATURE
<222> LOCATION: (10)..(10)
<223> OTHER INFORMATION: S-Sox
<220> FEATURE:
<221> NAME/KEY: MISC_FEATURE
<222> LOCATION: (12)..(12)
<223> OTHER INFORMATION: amide terminus

<400> SEQUENCE: 5

Ala His Leu Gln Arg Gln Leu Ser Ile Cys His His
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetyl
<220> FEATURE:
<221> NAME/KEY: MISC_FEATURE
<222> LOCATION: (10)..(10)
<223> OTHER INFORMATION: S-Clk
```

```
<220> FEATURE:
<221> NAME/KEY: MISC_FEATURE
<222> LOCATION: (12)..(12)
<223> OTHER INFORMATION: amide terminus

<400> SEQUENCE: 6

Ala His Leu Gln Arg Gln Leu Ser Ile Cys His His
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetyl
<220> FEATURE:
<221> NAME/KEY: MISC_FEATURE
<222> LOCATION: (4)..(4)
<223> OTHER INFORMATION: S-Sox
<220> FEATURE:
<221> NAME/KEY: MISC_FEATURE
<222> LOCATION: (15)..(15)
<223> OTHER INFORMATION: amide terminus

<400> SEQUENCE: 7

Ala Glu Glu Cys Ile Tyr Gly Glu Phe Glu Ala Lys Lys Lys Lys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-acetyl
<220> FEATURE:
<221> NAME/KEY: MISC_FEATURE
<222> LOCATION: (4)..(4)
<223> OTHER INFORMATION: S-Clk
<220> FEATURE:
<221> NAME/KEY: MISC_FEATURE
<222> LOCATION: (15)..(15)
<223> OTHER INFORMATION: amide terminus

<400> SEQUENCE: 8

Ala Glu Glu Cys Ile Tyr Gly Glu Phe Glu Ala Lys Lys Lys Lys
1               5                   10                  15
```